(12) United States Patent
Asahara et al.

(10) Patent No.: US 9,557,327 B2
(45) Date of Patent: Jan. 31, 2017

(54) DNA CONTROLLING MIR-140 EXPRESSION, AND SCREENING METHOD OF DRUGS USING SAID DNA

(71) Applicants: NATIONAL CENTER FOR CHILD HEALTH AND DEVELOPMENT, Tokyo (JP); NIPPON ZOKI PHARMACEUTICAL CO., LTD., Osaka-shi, Osaka (JP)

(72) Inventors: Hiroshi Asahara, Tokyo (JP); Satoshi Yamashita, Tokyo (JP); Mitsuru Naiki, Kato (JP); Kentaro Abe, Kato (JP)

(73) Assignees: NATIONAL CENTER FOR CHILD HEALTH AND DEVELOPMENT, Tokyo (JP); NIPPON ZOKI PHARMACEUTICAL CO., LTD., Osaka-shi (JP)

( * ) Notice: Subject to any disclaimer, the term of this patent is extended or adjusted under 35 U.S.C. 154(b) by 0 days.

(21) Appl. No.: 14/388,609

(22) PCT Filed: Apr. 2, 2013

(86) PCT No.: PCT/JP2013/060111
§ 371 (c)(1),
(2) Date: Sep. 26, 2014

(87) PCT Pub. No.: WO2013/151058
PCT Pub. Date: Oct. 10, 2013

(65) Prior Publication Data
US 2015/0056630 A1    Feb. 26, 2015

(30) Foreign Application Priority Data
Apr. 3, 2012 (JP) ................................. 2012-084950

(51) Int. Cl.
| | | |
|---|---|---|
| *C12N 15/11* | (2006.01) | |
| *G01N 33/53* | (2006.01) | |
| *C12N 15/113* | (2010.01) | |
| *A01K 67/027* | (2006.01) | |

(52) U.S. Cl.
CPC ....... *G01N 33/5308* (2013.01); *A01K 67/0275* (2013.01); *C12N 15/113* (2013.01); *A01K 2217/05* (2013.01); *A01K 2227/105* (2013.01); *A01K 2267/03* (2013.01); *C12N 2310/141* (2013.01); *G01N 2400/10* (2013.01); *G01N 2500/02* (2013.01); *G01N 2500/04* (2013.01); *G01N 2500/10* (2013.01)

(58) Field of Classification Search
CPC .......................... C12N 15/113; G01N 33/5308
See application file for complete search history.

(56) References Cited

U.S. PATENT DOCUMENTS

| | | | | |
|---|---|---|---|---|
| 2005/0228172 | A9 | 10/2005 | Wang | |
| 2005/0255487 | A1* | 11/2005 | Khvorova | A61K 31/713 435/6.11 |
| 2006/0134663 | A1* | 6/2006 | Harkin | C12Q 1/6886 435/6.11 |
| 2009/0018031 | A1* | 1/2009 | Trinklein | C12N 15/1051 506/10 |
| 2010/0081201 | A1* | 4/2010 | Simpson | A01K 67/0275 435/455 |

FOREIGN PATENT DOCUMENTS

| | | |
|---|---|---|
| EP | 2 021 499 A2 | 2/2009 |
| WO | 2007/078599 A2 | 7/2007 |

OTHER PUBLICATIONS

Robert Symons (Nucleic Acid Probes, CRC Press Boca Raton, Florida, 1989, Chapter 1, pp. 1-31.*
Yang et al., "MiR-140 is co-expressed with *Wwp2*-C transcript and activated by Sox9 to target *Sp 1* in maintaining the chondrocyte proliferation," *FEBS Letters*, 2011, vol. 585, pp. 2992-2997.
Lefebvre et al., "A new long form of Sox5 (L-Sox5), Sox6 and Sox 9 are coexpressed in chondrogenesis and cooperatively activate the type II collagen gene," *The EMBO Journal*, 1998, vol. 17, No. 19, pp. 5718-5733.
Han et al., "L-Sox5 and Sox6 Drive Expression of the Aggrecan Gene in Cartilage by Securing Binding of Sox9 to Far-Upstream Enhancer," *Molecular and Cellular Biology*, 2008, vol. 28, No. 16, pp. 4999-5013.
Smits et al., "The Transcription Factors L-Sox5 and L-Sox6 Are Essential for Cartilage Formation," *Developmental Cell*, 2001, vol. 1, pp. 277-290.
Lefebvre et al., "L-Sox5, Sox6 and Sox 9 control essential steps of the chondrocyte differentiation pathway," *Osteoarthritis and Cartilage*, 2001, vol. 9, Supplement A, pp. S69-S75.
Bernard et al., "Dimerization of SOX9 is required for chondrogenesis, but not for sex determination," *Human Molecular Genetics*, 2003, vol. 12, No. 14, pp. 1755-1765.
Akiyama et al., "The transcription factor Sox9 has essential roles in successive steps of the chondrocyte differentiation pathway and is required for expression of *Sox5* and *Sox6*," *Genes and Development*, 2002, vol. 16, pp. 2813-2828.
International Search Report issued in International Patent Application No. PCT/JP2013/060111 mailed Jun. 18, 2013.

(Continued)

*Primary Examiner* — Brian Whiteman
(74) *Attorney, Agent, or Firm* — Oliff PLC

(57) ABSTRACT

An object of the present invention is to provide DNA which regulates the expression of miR-140, a reporter vector which contains the DNA, cells and animals into which the reporter vector is introduced and a screening system for drugs which control the expression of miR-140 and is also to contribute in the development of new therapeutic agents for cartilage diseases such as osteoarthritis and intervertebral disk degeneration using the screening system. The DNA sequence according to the present invention is able to express any gene in a site where miR-140 is expressed and, in addition, it is also able to be utilized for screening a drug which regulates the expression of miR-140. Moreover, the drug that is selected by the screening system of the present invention is expected as a therapeutic agent for cartilage diseases accompanied by abnormality of cartilage.

17 Claims, 6 Drawing Sheets

(56) References Cited

OTHER PUBLICATIONS

Aug. 26, 2015 European Extended Search Report issued in European Patent Application No. 13772453.0.
Yukio Nakamura et al. "Sox9 Is Upstream of MicroRNA-140 in Cartilage." vol. 166. pp. 64-71. Appl Biochem Biotechnol (2012).
Satoshi Yamashita et al. "L-Sox5 and Sox6 Proteins Enhance Chondrogenic miR-140 MicroRNA Expression by Strengthening Dimeric Sox9 Activity." vol. 287 No. 26 pp. 22206-22215. The Journal of Biological Chemistry Jun. 22, 2012. The American Society for Biochemistry and Molecular Biology, Inc.

\* cited by examiner

Fig. 7

```
mouse    1  cagct-------cctcc---aactt---ttc-----------aggcttc            35
            .||||       |||| .||||  |||             ||||  |
human    1  gagcttccccaacctccgtgcacttgcattctgtgtgggcaggaggc--c            48 mouse   26  ctttg---tgaaa-ggggccctatcccatcaaggaacctatggtttcaag            71
            |  ||   ||||| ||||| |  |||  |||| ||.|||||||||||||
human   49  c---tgccctgaaagggggctccgtcctgtcaa-gagcctatggtttcaag           95 mouse   72  actta--------ctgttggaa-ttacttggaagaggagcctgtgttgcca          113
            |||||        .|||||||| ||.|||||||||.|||||||||||||||
human   96  acttaaacatctttgttggaacttgcttggaagaggggcctgtgttgcca          145 mouse  114  ccttgggaagaaagtttctctgtcccttcagttgggggtagcgggagggc          163
            ||||||.||||||||||||||||||||.||||| .|||||| . |||||||
human  146  ccttggaaagaaagtttctctgtcctttcagctgggggtggagggaggc           195 mouse  164  t---gcagtgggcttggctggcagtggag---caccactggtatttgcac          207
            |   |.||.||||| ||||||||||.|||   |||||.|| |||.|.|
human  196  tgtggaaggggggctt-gctggcagttgagttccaccaatg---ttttctc          241 mouse  208  aaggctggactgagcccattcatcgtcctgctgctgtgtgcggatctgt           257
            |||.|.|.|||||||||||||||||.|||||| |..||||.|||||.|.
human  242  aagccgacactgagcccattcatcctcctgc--ccatgtgtggctccgg          289 mouse  258  catcccagatggagccag-ccag--gtct        284   (SEQ ID No. 5)
            ||.|||.|||.||.||||| ||||  |.||
human  290  caccctagacggggccagcccagcagcct        319   (SEQ ID No. 6)
```

DNA CONTROLLING MIR-140 EXPRESSION, AND SCREENING METHOD OF DRUGS USING SAID DNA

TECHNICAL FIELD

The present invention relates to DNA which regulates the expression of miR-140, to a reporter vector containing the DNA, to cells and animals into which the reporter vector is introduced, to a method for screening a drug utilizing the DNA, etc.

BACKGROUND ART

Micro RNA (miRNA) is a small RNA comprising 20 to 23 bases and being untranslated into protein and, up to now, 1,000 or more kinds of miRNA have been identified on human genome. miRNA is produced in such a manner that, after transcribed from genome as primary miRNA (pri-miRNA) in several hundreds to several thousands of base length, it is cleaved by enzymes called Drosha and DGCR8 into a precursor miRNA (pre-miRNA) having stem loop structure comprising about 70 base pairs followed by treating with Dicer and TRBP/PACT whereupon miRNA is produced as a double-stranded RNA comprising 20 to 23 base pairs. The produced miRNA is incorporated into a protein complex called RNA-induced silencing complex (RISC), binds mainly to target mRNA having complementary sequence in the 3' untranslated region and suppresses the expression of target mRNA through the activity of Argonaute acting as a functional domain of RISC. One miRNA has several hundreds kinds of mRNA complementary sequences in the 3' untranslated region and miRNA is able to regulate a plurality of gene expressions at the same time. It has been becoming clear that some miRNA shows a tissue-specific expression mode, participates in generation of tissues and organs thereof and involves in various bio-function and development of disease such as immunity, oncogenesis, aging, etc.

miR-140 is one of miRNA which has been reported to express specifically to the cartilage forming region in a developing period of mice and is coded to intron 16 of the gene of WW domain containing E3 ubiquitin protein ligase 2 (Wwp2). miR-140 specifically rises its expression together with cartilage differentiation from mesenchymal cells. miR-140 also plays an important role in differentiation and homeostasis maintenance of cartilage in, for example, such a manner that a miR-140-deleted knockout mouse results in abnormality in chondrocyte growth in endochondral ossification. Moreover, in osteoarthritis which is a cartilage degenerative disease in a joint, expression of miR-140 in chondrocytes specifically decreases. In view of the fact that a miR-140 knockout mouse shows a morbid state like osteoarthritis and that a transgenic mouse where miR-140 is excessively expressed shows a resistance to osteoarthritis, miR-140 is deeply participated in occurrence of cartilage degenerative disease. Accordingly, a drug exhibiting the activity of regulating the expression of miR-140 is expected as a therapeutic agent for cartilage degenerative diseases such as osteoarthritis or intervertebral disk degeneration. However, due to the reason that the regulation mechanism of miR-140 is not clear, it has been difficult to screen a drug having the activity of regulating its expression.

Incidentally, Sox9 which is one of transcription factors plays an important role for controlling the chondrocyte differentiation. During the chondrogenesis, Sox9 is expressed in all of chondrocyte progenitors and chondrocytes but the expression dramatically decreases in hypertrophic chondrocytes. In an expression regulatory region for structural gene such as type 2 collagen (Col2a1) or aggrecan (Agcl) which is a main constitute of cartilage, consensus sequence (A/T)(A/T) CAA (T/A) G to which Sox9 binds is present and, when Sox9 binds to this region, expression of each gene is induced and cartilage differentiation is promoted. Moreover, although it has been known that, in cartilage differentiation, L-Sox5 and Sox6 which are other transcription factors work cooperatively with Sox9 to promote the cartilage differentiation, genes which are targets thereof have not been made clear except Col2a1 and Agcl and the regulatory mechanism where they potentiate the function of Sox9 has not been made clear yet.

In Non-Patent Document 1, Yang et al report that transcription start site for pri-miR140 exists in intron 10 of Wwp2 gene, that a luciferase reporter vector is constructed using a 2 kbp upstream region of pri-miR140 and that Sox9 regulates miR-140 expression in the region. Yang et al further found two Sox9-binding sites in the region (CAGGTTCCTTTGT in −824 bp upstream region of pri-iR140 and TAAAGGTGCTTTGT in −200 bp upstream region thereof) and made clear that, when mutation is introduced into the binding site at −200 bp, the reporter activity significantly decreases. However, Non-Patent Document 1 does not mention the cooperative action of Sox9 with Sox5 and Sox6 and neither mentions nor even suggests to apply those binding regions and reporter vector binding to those regions for a drug screening. In addition, the DNA sequence of the regions other than the above-mentioned two Sox9-binding sites is not disclosed in Non-Patent Document 1.

PRIOR ART DOCUMENT

Non-Patent Document

Non-Patent Document 1: Yang, et al. MiR-140 is co-expressed with Wwp2-C transcript and activated by Sox9 to target Sp1 in maintaining the chondrocyte proliferation. (2001). FEBS Letter 585, 2992-2997

SUMMARY OF THE INVENTION

Problems to be Solved by the Invention

An object of the present invention is to provide DNA which regulates the expression of miR-140, a reporter vector which contains the DNA, cells and animals into which the reporter vector is introduced and a screening system for drugs which regulate the expression of miR-140. Another object is to contribute in the development of new therapeutic agent for cartilage degenerative diseases such as osteoarthritis and intervertebral disk degeneration using the screening system.

Means for Solving the Problems

The present inventors have independently found by a rapid amplification of cDNA ends (RACE) method that a transcription start site (TSS) of pri-miR-140 exists in intron 10 of Wwp-2 gene and cloned the region of about 3 kbp upstream of TSS (miR140-3k, SEQ ID No. 10) to a pGL4.12 luc2CP vector having firefly luciferase as a reporter gene to prepare a reporter vector pGL4-miR140-3k. The pGL4-miR140-3k was transfected to 293T cell together with Sox9 expression vector to measure the reporter activity whereupon the luciferase activity increased depending upon the amount of transfected Sox9 expression vector whereby it was suggested that a regulation element of Sox9 was present in the region (FIG. 1). After that, combinations of expression vectors Sox9, L-Sox5 and Sox6 (Sox-trio) were investigated and, since L-Sox5 and Sox6 further increased the pGL4-miR140-3k reporter activity by Sox9, it was shown that L-Sox5 and Sox6 regulated the expression of miR-140 in cooperation with Sox9 (FIG. 2). In transgenic mouse fetuses of E12.5 and E15.5 day prepared by using a pGL4-miR140-LacZ reporter vector prepared by replacement of a reporter of pGL4-miR140-3k from luciferase to LacZ, cartilage tissues such as ribs and vertebrae in addition to forelimbs and hind limbs are stained by means of X-gal staining showing LacZ activity whereby it has been clarified that such a region is an expression regulatory region for miR-140 which is specifically expressed in cartilage (FIG. 8).

In order to identify the region regulated by Sox-trio in miR140-3k, upstream-1 kbp, -0.8 kbp, -0.7 kbp, -0.6 kbp, -0.5 kbp, -0.4 kbp and -0.3 kbp regions of TSS of miR-140 were cloned to pGL4.12 luc2CP vector to prepare reporter vectors (left side, FIG. 3). An increase of luciferase activity by L-Sox5, Sox6 and Sox9 was investigated whereupon, in pGL4-miR140-1k, an increase in luciferase activity in the similar extent as pGL4-miR140-3k was observed (right side, FIG. 3). In pGL4-miR140-0.8k and pGL4-miR140-0.7k, luciferase activity of the cell into which L-Sox5, Sox6 and Sox9 were transfected decreased as compared with pGL4-miR140-3k but luciferase activity of the cell into which only Sox9 was transfected was in the same extent as pGL4-miR140-3k (right side, FIG. 3). In pGL4-miR140-0.6k, pGL4-miR140-0.5k, pGL4-miR140-0.4k and pGL4-miR140-0.3k, significant decrease was noted in luciferase activity of the cell into which only Sox9 was transfected (right side, FIG. 3). In view of those results, it was suggested that the DNA sequence (SEQ ID No. 5) of −936~−652 bp upstream region from TSS is an important region for regulation of miR-140 expression by L-Sox5, Sox6 and Sox9 and that a sequence essential for the cartilage-specific expression is present in the sequence (miR140-PSB, SEQ ID No. 3) between −739 and −652 bp. When the sequence between −739 bp~−652 bp was precisely checked, there was found a palindromic Sox9 binding consensus motif in the DNA sequence (uppermost line in a frame of FIG. 4, SEQ ID No. 1).

When a reporter vector was prepared by means of mutation introduction into the above palindromic Sox9 binding motif of miR140-PSB using by Site directed mutagenesis method, an increase in luciferase activity of miR140-PSB by L-Sox5, Sox6 and Sox9 disappeared by the mutation introduction (FIG. 5). Further, when a radioisotope (RI)-labeled probe was synthesized where the same mutation was introduced into palindromic Sox9 binding motif of miR140-PSB and its binding property to Sox9 was investigated by an Electrophoretic Mobility Shift Assay (EMSA), shift of the band was observed when mutation was introduced into 5'-site of the palindromic Sox9 binding sequence but, when mutation was introduced into 3'-site or both sites, shift of the band disappeared. In view of those results, it was clarified that Sox9 was bound to a palindromic Sox9 binding sequence identified in the present invention whereby miR-140 expression is regulated (FIG. 6). The Sox9 binding sequence identified in the present invention is a novel one being different from the Sox9 binding sequence which has been already reported as a consensus sequence.

Incidentally, when the DNA sequence (SEQ ID No. 5) of −936 bp to −652 bp upstream region from TSS of the mouse was compared (alignment) with human homologous sequence (SEQ ID No. 6), the homology between both sequences was 71.5% (236 bases in 330 bases were identical) (FIG. 7). Among the above, in the Sox binding sequences (SEQ ID Nos. 1 and 2 in a frame of FIG. 7) identified in the present invention, 16 bases in 17 bases were identical (94.1%). Further, homology of the 87 bp region of the above miR140-PSB (SEQ ID No. 3) with the human homologous sequence (SEQ ID No. 4) was 72.2% (65 bases in 90 bases were identical).

The regions of −3 kbp and −0.7 kbp upstream regions from human TSS including the above human homologous sequence were cloned from human genome genes to prepare a reporter vector in the same manner as in the above mouse genome region and the increases in luciferase activity by L-Sox5, Sox6 and Sox9 were investigated whereupon the same result as in the corresponding mouse reporter vector was resulted (FIG. 9).

The present invention has been achieved on the basis of the above findings and is to provide DNA which regulates the expression of miR-140, a reporter vector containing the DNA, cells and animals into which the reporter vector is introduced and a method for screening a drug utilizing the DNA. To be more specific, the present invention provides the followings.

(1) DNA having the activity regulating the expression of miR-140 and being mentioned in any of the following (a) to (g).

(a) DNA comprising a base sequence of SEQ ID No. 1 or 2.

(b) DNA comprising a base sequence of SEQ ID No. 3 or 4 containing the base sequence of SEQ ID No. 1 or 2.

(c) DNA comprising a base sequence of SEQ ID No. 5 or 6 containing the base sequence of SEQ ID No. 1 or 2.

(d) DNA comprising a base sequence of any of SEQ ID Nos. 7 to 10, 40 and 41 containing the base sequence of SEQ ID No. 1 or 2.

(e) DNA comprising a base sequence where one or two base(s) is/are substituted, deleted, added and/or inserted in the base sequence of the DNA of the above (a).

(f) DNA containing the base sequence of the DNA of the above (a) or (e) as a repeating sequence for two to five times.

(g) DNA comprising a base sequence being modified within an extent of homology of 60% or more to the DNA of any of the above (b) to (d) and (f) as a result of such a means that, in a base sequence of the above DNA, one or more base(s) is/are substituted, deleted, added and/or inserted.

(2) The DNA according to (1) being mentioned in (a) or (e).

(3) The DNA according to (1) being mentioned in (f).

(4) The DNA according to (1) being mentioned in (b) or (g).

(5) The DNA according to (1) being mentioned in (c) or (g).

(6) The DNA according to (1) being mentioned in (d) or (g).

(7) DNA where its range of homology to the DNA of any of (1) and (4) to (6) is 65% or more.

(8) DNA where its range of homology to the DNA of any of (1) and (4) to (6) is 70% or more.

(9) A vector containing the DNA of any of (1) to (8).

(10) The vector according to (9), wherein a reporter gene functionally binds to downstream of the DNA of any of (1) to (8).

(11) The vector according to (10), wherein the reporter gene is LacZ, β-glucosidase, β-glucuronidase, alkaline phosphatase, chloramphenicol acetyl transferase (CAT), luciferase or fluorescent protein.

(12) The vector according to (11), wherein the reporter gene is LacZ, luciferase or fluorescent protein.

(13) A cell into which the vector of any of (9) to (12) is introduced.

(14) The cell according to (13), wherein the cell is any cell selected from the group consisting of 293T cell, ATDC5 cell, SW1353 cell, primarily cultured chondrocyte, mesenchymal stem cell and embryonic stem cell (ES cell).

(15) An animal (excluding human) into which the vector of any of (9) to (12) is introduced.

(16) The animal according to (15), wherein the animal (excluding human) is a mouse or a rat.

(17) A method for screening a drug which regulates the expression of miR-140 using the cell of (13) or (14).

(18) A method for screening a drug which regulates the expression of miR-140 comprising:

(a) a step where a drug is made to contact with the cell of (13) or (14), (b) a step where a reporter activity in the cell is detected and (c) a step of selecting a drug which increases or decreases the reporter activity by comparing with the control detected in the absence of a drug.

(19) A method for screening a drug which regulates the expression of miR-140 using the DNA of any of (1) to (8).

(20) A method for screening a drug which regulates the expression of miR-140 comprising (a) a step where L-Sox5, Sox6 and/or Sox9 protein(s) is/are made to contact with the DNA of any of (1) to (8), (b) a step where a binding of the DNA to the protein(s) is detected and (c) a step of selecting a drug which has the activity of potentiating or attenuating the binding of the DNA to the protein by comparing with the control value detected in the absence of a drug.

(21) The method according to (20), wherein the detection in the step (b) is a gel shift assay.

(22) A method for screening a drug which regulates the expression of miR-140 using a cell into which a vector where DNA having a base sequence regulating the expression of miR-140 functionally binds to upstream region of a reporter gene is introduced.

(23) The method according to (22), wherein a method for screening a drug regulating the expression of miR-140 comprises (a) a step where a drug is made to contact with the cell, (b) a step where a reporter activity in the cell is detected and (c) a step of selecting a drug which increases or decreases the reporter activity by comparing with the control detected in the absence of a drug.

(24) A method for screening a drug which regulates the expression of miR-140 using the DNA which has a base sequence regulating the expression of miR-140.

(25) The method according to (24), wherein a method for screening a drug which regulates the expression of miR-140 comprises (a) a step where L-Sox5, Sox6 and/or Sox9 protein(s) is/are made to contact with the DNA, (b) a step where a binding of the DNA to the protein(s) is detected and (c) a step of selecting a drug which has the activity of potentiating or attenuating the binding of the DNA to the protein(s) by comparing with the control detected in the absence of a drug.

(26) The method according to (25), wherein the detection in the step (b) is a gel shift assay.

(27) A method for study, determination or evaluation of a drug to the expression of miR-140 using an animal (excluding human) into which a vector where DNA having a base sequence regulating the expression of miR-140 functionally binds to upstream region of a reporter gene is introduced.

(28) The method according to any of (22) to (27), wherein the DNA is such a DNA of any of the following (a) to (c).

(a) DNA comprising a base sequence of SEQ ID No. 1 or 2.

(b) DNA comprising a base sequence where one or two base(s) is/are substituted, deleted, added and/or inserted in the base sequence of DNA of (a).

(c) DNA containing the base sequence of DNA of (a) or (b) as a repeating sequence for two to five times.

(29) The method according to any of (22) to (27), wherein the DNA is such a DNA of the following (a) or (b).

(a) DNA comprising a base sequence of SEQ ID No. 3 or 4 containing a base sequence of SEQ ID No. 1 or 2.

(b) DNA comprising a base sequence being modified to an extent of homology of 60% or more, preferably 65% or more or, more preferably, 70% or more to the following DNA by such a means that one or more base(s) is/are substituted, deleted, added and/or inserted in the base sequence of DNA of (a).

(30) The method according to any of (22) to (27), wherein the DNA is such a DNA of the following (a) or (b).

(a) DNA comprising a base sequence of SEQ ID No. 5 or 6 containing a base sequence of SEQ ID No. 1 or 2.

(b) DNA comprising a base sequence being modified to an extent of homology of 60% or more, preferably 65% or more or, more preferably, 70% or more to the following DNA by such a means that one or more base(s) is/are substituted, deleted, added and/or inserted in the base sequence of DNA of (a).

(31) The method according to any of (22) to (27), wherein the DNA is such a DNA of the following (a) or (b).

(a) DNA comprising a base sequence of any of SEQ ID Nos. 7 to 10, 40 and 41 containing a base sequence of SEQ ID No. 1 or 2.

(b) DNA comprising a base sequence where one or two base(s) is/are substituted, deleted, added and/or inserted in the base sequence of DNA of (a).

(32) The method according to any of (22), (23) and (27), wherein the reporter gene is LacZ, β-glucosidase, β-glucuronidase, alkaline phosphatase, chloramphenicol acetyl transferase (CAT), luciferase or fluorescent protein.

(33) The method according to (32), wherein the reporter gene is LacZ, luciferase or fluorescent protein.

(34) The method according to (22) or (23), wherein the cell is any cell selected from the group consisting of 293T cell, ATDC5 cell, SW1353 cell, primarily cultured chondrocyte, mesenchymal stem cell and embryonic stem cell (ES cell).

(35) The method according to (27), wherein the animal (excluding human) is a mouse or a rat.

(36) A drug which is selected by the method of any of (17) to (35).

(37) The drug according to (36), wherein it is a synthetic compound.

Advantages of the Invention

The DNA sequence having the activity which can regulate the expression of miR-140 in accordance with the present invention is able to express any gene in the site where miR-140 is expressed and, in addition thereto, it is also able to be utilized for screening of a drug which regulates the expression of miR-140. Moreover, a drug selected by the screening system of the present invention is expected as being useful as a treating agent for cartilage diseases such as osteoarthritis and intervertebral disk degeneration accompanied by abnormality of cartilage whereby the present invention is of very high utility in industry.

BRIEF DESCRIPTION OF THE DRAWINGS

FIG. 7 is the result of comparison (alignment) of the miR-140 regulatory region of a mouse with human homologous sequence.

MODE FOR CARRYING OUT THE INVENTION

Figure 1:
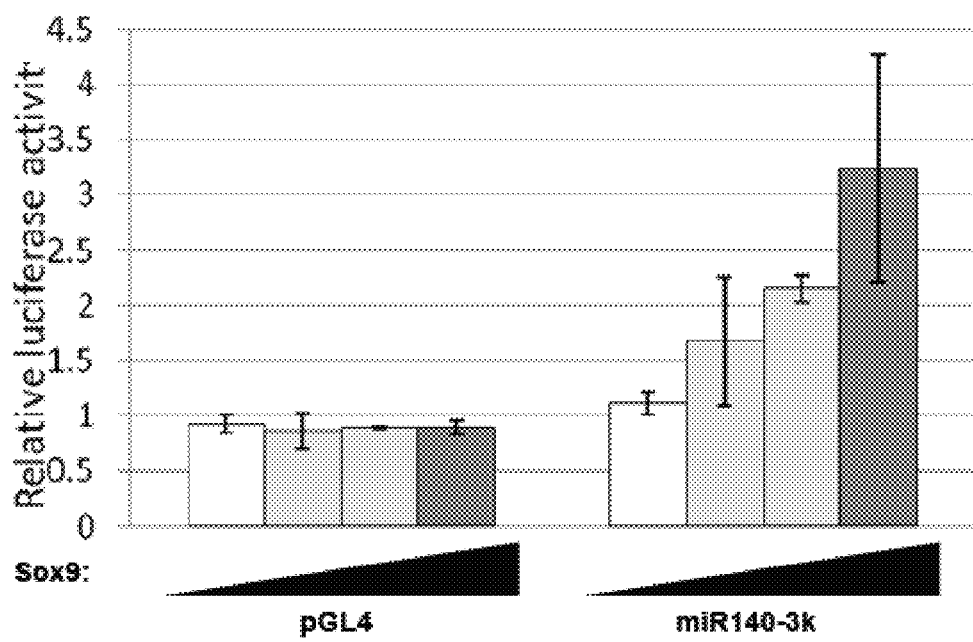
FIG. 1 is the result of evaluation of influence of the co-transfected Sox9 expression vector amount on the luciferase activity of 293T cell into which pGL4-miR140-3k or pGL4 of a vehicle vector is transfected.

The present invention relates to DNA that regulates the expression of miR-140, to a reporter vector containing the DNA, to a cell and an animal into which the reporter vector is introduced, to a method for screening a drug utilizing the DNA, etc.

The present invention provides DNA that regulates the expression of miR-140. As the minimum unit, the DNA contains the sequence of SEQ ID No. 1 or 2, preferably the sequence of SEQ ID No. 3 or 4 or, more preferably, the sequence of SEQ ID No. 5 or 6, which is the expression regulatory region of miR-140 containing Sox9 binding sequence or, alternately, it may be any of the DNA of SEQ ID No. 7 to 10, 40 and 41 which will be mentioned later. Further, the DNA of the present invention may be such a DNA comprising a base sequence being modified to an extent of homology of 60% or more, preferably 65% or more or, more preferably, 70% or more to the following DNA by such a means that one or more base(s) is/are substituted, deleted, added and/or inserted in the base sequence of DNA of any of SEQ ID Nos. 1 to 6. Still further, the DNA of the present invention may be such a DNA comprising a base sequence where one or more base(s) of the DNA of any of SEQ ID Nos. 7 to 10, 40 and 41 is/are substituted, deleted, added and/or inserted. Although the DNA as such can be obtained from animals as a whole regardless of the species, it is preferably obtained from mammals and, more preferably, from mouse or human.

The present invention provides a vector containing the above DNA. Although the vector may be in any type such as plasmid or virus, it is a vector containing the above DNA sequence being independently duplicated in cells of *Escherichia coli* and/or mammals and having a general-purpose selective marker which functions in the cells of *Escherichia coli* and/or mammals. When the sequence of SEQ ID No. 1 or 2 which is a Sox9 binding sequence is applied as DNA, it may be used in a vector as a repeating sequence as needed.

Although there is no particular limitation for the above selective marker, advantageous examples thereof include a drug resistance gene to hygromycin, neomycin, puromycin, etc.

The present invention provides a vector (reporter vector) where a reporter gene being commonly used for the downstream region of the above DNA functionally binds thereto.

Although there is no particular limitation for the above reporter gene, advantageous examples thereof include fluorescent protein gene such as Venus, AcGFP1, AmCyan1, AsRed, BFP, CFP, dsRed, EBFG, ECFP, EGFP, EYFP, F1AsH, GFP, HcRed1, mBanana, mCherry, mOrange, mRFP1, mPlum, mRaspberry, mStrawberry, PhiYFP, RFP, tdTomato, YEP, ZsGreen1 or ZsYellow1; luciferase gene such as firefly luciferase, Renilla luciferase, Metridia luciferase, Gaussia luciferase or Cypridina luciferase; and enzyme gene such as LacZ, β-glucuronidase, β-glucosidase, alkaline phosphatase, chloramphenicol acetyl transferase (CAT) or catalase.

The present invention provides a cell into which the above reporter vector is introduced. Although there is no particular limitation for the cell into which the above reporter vector is introduced, it may be selected from primarily cultured cells separated from animal tissues, commonly used established cell line, etc. or preferably selected from 293T cell, ATDC5 cell, SW1353 cell, primarily cultured chondrocyte, mesenchymal stem cell, embryonic stem cell (ES cell), etc.

Although there is no particular limitation for introduction method of a reporter vector into the cell, it may be carried out by commonly used methods such as electroporation method, calcium phosphate method, DEAE dextran method, cationic liposome method and lipofection method.

The present invention provides an animal into which the above reporter vector is introduced. Although there is no particular limitation for the animal into which the above reporter vector is introduced, all animals excluding human that are able to prepare transgenic animals may be selected and, preferably, mice, rats, etc. may be selected.

The above animal may be prepared by a known method such as that ES cell into which the above reporter vector is introduced is prepared and then the ES cell is injected into fertilized egg by a fertilized egg pronuclear injection method.

The above animal is useful for evaluating the effect of a drug in vivo to the expression of miR-140. To be more specific, expression of miR140 in cartilage tissues of the drug treated animal can be evaluated by a reporter activity. A drug that strongly activates reporter gene can be expected for its effect as a treating agent for cartilage diseases.

The present invention provides a method for screening a drug that regulates the expression of miR-140 using the above cell. To be more specific, the cell is made to contact with a drug and allowed to stand for predetermined time and then a reporter activity of the cell is measured and compared with a negative control being detected in the absence of the drug whereby a drug having an activity of increasing or decreasing the expression of miR-140 can be selected. In that case, L-Sox5, Sox6 and/or Sox9 may be also co-expressed in the cell. There is no particular limitation for the drug and examples thereof include cell extract, supernatant liquid of cultured cell, animal tissue extract, fermentative microbe product, marine organism extract, plant extract, purified or roughly-purified protein, nucleic acid, oligonucleotide, expression vector, synthetic compound (including low-molecular compound and high-molecular compound), natural compound, etc.

The present invention provides a method for screening a drug that regulates the expression of miR-140 using the above DNA. To be more specific, L-Sox5, Sox6 and/or Sox9 protein(s) is/are made to contact with the DNA in the co-presence of a testing substance, binding of the DNA to the protein is detected and comparison with the control detected in the absence of a drug is conducted whereupon a drug having the activity of potentiating or attenuating the binding of the DNA to the protein can be selected. There is no particular limitation for the drug and examples thereof include cell extract, supernatant liquid of cultured cell, animal tissue extract, fermentative microbe product, marine organism extract, plant extract, purified or roughly-purified protein, nucleic acid, oligonucleotide, expression vector, synthetic compound (including low-molecular compound and high-molecular compound), natural compound, etc.

Binding of the DNA to the protein mentioned above can be detected by an electrophoretic mobility shift assay (EMSA) method. Thus, the DNA labeled with radioisotope, digoxigenin, biotin or the like is used as a probe so that the protein is made to contact therewith, then electrophoresis is carried out and the binding activity is detected as the shift of the band of a probe. At that time, it is also possible that an antibody to the protein is further made to contact therewith to detect the supershift. The EMSA method is also called a gel shift assay.

The present invention provides a drug that is selected by the above screening method. Since miR-140 plays an important role for the differentiation of cartilage or for the homeostasis of cartilage, there is a possibility that a drug selected by the screening method of the present invention is useful as a treating agent for cartilage diseases such as osteoarthritis and intervertebral disk degeneration.

EXAMPLES

The present invention will be more specifically illustrated by the following examples although the present invention shall not be limited thereto.

Example 1

Detection of Regulation of miR-140 Expression by Sox9

(1) Preparation of Reporter Vector

Polymerase chain reaction (PCR) was conducted using a forward primer containing KpnI cleavage site (AAGGTAC-CACTGTTCAGAAGGAGACTACTCTGTC) (SEQ ID No. 11) and a reverse primer containing XhoI cleavage site (GCACTCGAGACCGACCTCTGCTCAGCTC) (SEQ ID No. 12) where genomic DNA of incubated chondrocyte of G57BL/6 mice was used as a template whereby DNA fragments in the 3 kbp upstream region from the transcription start site of miR-140 were amplified. Thus, PrimeStar HS DNA polymerase (Takara Bio Inc.) was used as a DNA polymerase to prepare a reaction solution containing 1×PCR reaction solution, 0.2 mmol/L of dNTP, 0.2 µmol/L of each primer, 0.5 U of PrimeStar HS polymerase and 10 ng of genomic DNA, the reaction solution was heated at 98° C. for 2 minutes, then a cycle comprising 98° C. for 10 seconds, 60° C. for 5 seconds and 72° C. for 3 minutes was repeated for 30 times and a treatment at 72° C. for 7 minutes was conducted to carry out the PCR. The amplified DNA fragments were subjected to a restriction enzyme treatment using KpnI and XhoI in 1×M buffer. A pGL4.12 luc2CP vector (manufactured by Promega Corporation) having firefly luciferase gene as a reporter gene was similarly subjected to a restriction enzyme treatment. The amplified DNA fragments and pGL4.12 luc2CP vector were subjected to ligation using a DNA ligation kit (Takara Bio Inc.) and *Escherichia coli* made into competent cells was transformed to clone the vector into which the DNA fragment was incorporated. The cloned *Escherichia coli* was incubated to purify a plasmid DNA whereupon a reporter vector pLG4-miR140-3k was prepared.

(2) Reporter Assay 293T cells ($5 \times 10^4$ cells) were sown in each well of a 48-well plate and cultured using a DMEM medium containing 10% of fetal bovine serum (FBS) in an incubator setting to the condition of 37° C. and 5% $CO_2$. After 24 hours, to a 10 µl OPTI-MEM medium (manufactured by Life Technologies) were added 0, 50, 100 or 400 ng of pcDNA3-HA-Sox9 (expression vector of Sox9) and pcDNA3 (vehicle vector) were added so as to make 800 ng in total. Then, 100 ng of pGL4.12 (vehicle vector) or pGL4-miR140-3K, 10 ng of pRL-TK (manufactured by Promega Corporation) which is a vector having Renilla luciferase in a downstream region of HSV tyrosine kinase (TK) promoter and 1 µl of FuGENE HD Transfection Reagent (manufactured by Promega Corporation) were added thereto to incubate for 30 minutes at room temperature followed by adding to the incubated cells to transfect. After 48 hours, the culture liquid was removed and 40 µl of Dual-Glo Luciferase Reagent (manufactured by Promega Corporation) (a chemiluminescence substrate) was added thereto followed by subjecting to a reaction for 10 minutes. The reaction product was transferred to a 96-well plate and the luciferase activity derived from pGL4.12 or pGL4-miR14-3k was measured by Wallac 1420 ARVOx (manufactured by Amersham) (a chemiluminescence measuring device). After the measurement, 20 µl of Dual-Glo Stop & Glo Reagent (manufactured by Promega Corporation) was added and the mixture was incubated for 10 minutes at room temperature to measure the luciferase activity derived from pRL-TK. Each of the data was standardized by dividing the luciferase activity derived from pGL4.12 or pGL4-miR140-3k by the luciferase activity derived from pRL-TK whereupon mean value and standard deviation of the independently conducted three experiments were calculated.

(3) Results

Results of this Example are shown in FIG. 1. In the cell into which pGL4-miR140-3k (upper line of FIG. 1) (a reporter vector containing DNA fragment (SEQ ID No. 10) of 3 kbp upstream region from the starting site of transcription of miR-140) was subjected to transfect, the luciferase activity increased depending upon the amount of the co-transfected Sox9 expression vector (the graph in right side, lower line, FIG. 1). On the contrary, in the cell into which pGL4.12 (a vehicle vector containing no DNA fragment of 3 kbp upstream region from the transcription start site of miR-140) was subjected to transfect, no luciferase activity increased even when the amount of the vector was increased (the graph in left side, lower line, FIG. 1). In view of the above results, it was found that the DNA fragment having the sequence of SEQ ID No. 9 obtained in this Example, the reporter vectors into which the DNA fragment is incorporated and the cells into which the reporter vector is introduced are useful for evaluating the action of the Sox9 expression vector on the expression regulation of miR-140.

Example 2

Regulation of Expression of miR-140 by L-Sox5, Sox6 and Sox9

(1) Reporter Assay 293T cells ($5 \times 10^4$ cells) were sown in each well of a 48-well plate and incubated using a DMEM medium containing 10% of FBS in an incubator setting to the condition of 37° C. and 5% $CO_2$. After 24 hours, to 10 μl of an OPTI-MEM medium were added each 50 ng of pcDNA3-HA-Sox5 (expression vector of L-Sox5), pcDNA3-HA-Sox6 (expression vector of Sox6) and/or pcDNA3-HA-Sox9 and pcDNA3 so as to make their total amount 150 ng. Then, 100 ng of pGL4.12 or pGL4-miR140-3K obtained in Example 1, 10 ng of pRL-TK and 1 μl of FuGENE HD Transfection Reagent were added followed by incubating for 30 minutes at room temperature and the mixture was added to the incubated cells to transfect. After 24 hours from the transfection, the luciferase activity was measured in the same manner as in (2) of Example 1.

(2) Results

Figure 2:
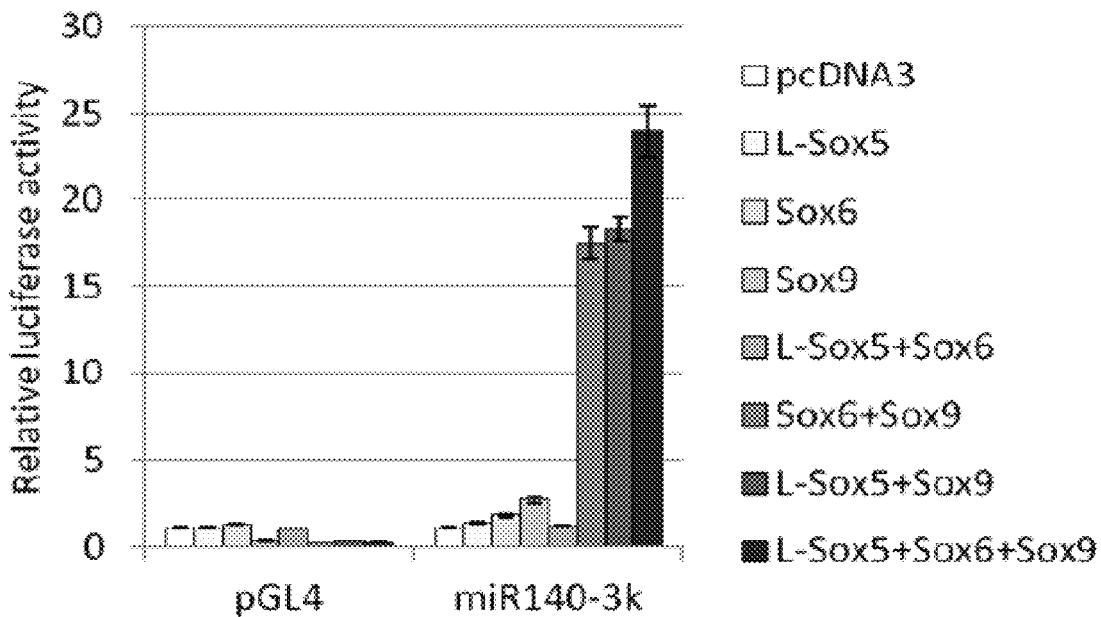
FIG. 2 is the result of evaluation of influence of a combination of co-transfected L-Sox5, Sox6 and/or Sox9 expression vector(s) on the luciferase activity of 293T cell into which pGL4-miR140-3k is transfected.

Results of the present Example are shown in FIG. 2. When pcDNA3 (vehicle vector) and either L-Sox5 expression vector or Sox6 expression vector or both L-Sox5 expression vector and Sox6 expression vector were transfected into the cell into which pGL4-miR140-3k was subjected to transfect, the luciferase activity did not increase. The luciferase activity of a cell into which Sox9 expression vector was transfected in the similar manner was high as compared with the case where pcDNA3 (vehicle vector) was transfected although the difference was only a little. However, the luciferase activity of a cell into which L-Sox5 expression vector or Sox6 expression vector was transfected together with Sox9 expression vector significantly increased as compared with the case of Sox9 expression vector only. The luciferase activity of a cell into which all of Sox9 expression vector, L-Sox5 expression vector and Sox6 expression vector were transfected was far higher as compared with the case of above cell into which Sox9 expression vector and L-Sox5 expression vector or Sox6 expression vector were transfected. On the contrary, in a cell into which pGL4.12 (a vehicle vector) was transfected, its luciferase activity did not increase even when any combination of Sox was transfected. In view of the above results, it was found that the DNA fragment having a sequence of SEQ ID No. 10 used in this Example, the reporter vectors into which the DNA fragment was incorporated and the cells into which the reporter vector was introduced are useful for evaluating the action to expression regulation of miR-140 by a combination of Sox9 expression vector, L-Sox5 expression vector and Sox6 expression vector.

Example 3

Analysis of Expression Regulatory Region of miR-140

(1) Preparation of Reporter Vector

PCR was carried out using any of forward primers in Table 1 including XhoI cleavage site and a reverse primer (GCAAGATCTACCGACCTCTGCTCAGCTC) (SEQ ID No. 20) containing BglII cleavage site and pGL4-miR140-3k as a template to amplify each DNA fragment. Thus, a reaction solution containing 1×PCR solution, 0.2 mmol/L dNTP, 0.2 μmol/L of each primer, 0.5 U of PrimeStar HS DNA polymerase and 10 ng of pGL4-miR140-3k was prepared, heated at 98° C. for 2 minutes, subjected to 30 cycles each comprising 98° C. for 10 seconds, 60° C. for 5 seconds and 72° C. for 1 minute, and subjected to a treatment at 72° C. for 7 minutes to conduct a PCR. The amplified DNA fragment was subjected to a restriction enzyme treatment using XhoI and BglII in 1×H buffer. A pGL4.12 luc2CP vector having luciferase gene as a reporter was similarly subjected to a restriction enzyme treatment. The amplified DNA fragment was ligated into the pGL4.12 luc2CP vector using a ligation mix and *Escherichia coli* made into competent cells was transformed to clone the vector into which the DNA fragment was incorporated. *Escherichia coli* after the cloning was incubated to purify a plasmid DNA whereupon a reporter vector of Table 1 was prepared (left side of FIG. 3).

TABLE 1

| Reporter Vector | Forward primer including XhoI cleavage site | SEQ ID No. |
|---|---|---|
| pGL4-miR140-1k | GAACTCGAGCAGCTCCTCCAACTTTTCAGG | 13 |
| pGL4-miR140-0.8k | GAACTCGAG GCCACCTTGGGAAGAAAGTT | 14 |
| pGL4-miR140-0.7k | GAACTCGAGGTATTTGCACAAGGCTGGAC | 15 |
| pGL4-miR140-0.6k | GAACTCGAGGCAGCCTGAAGTCTGCATTC | 16 |
| pGL4-miR140-0.5k | GAACTCGAGCCGAAGGCTACGAGGACTCT | 17 |
| pGL4-miR140-0.4k | GAACTCGAGGTGTAAATGGTGACCCTGACG | 18 |
| pGL4-miR140-0.3k | GAACTCGAGAACACTGAGCAACTTGAGG | 19 |

(2) Measurement of Reporter Activity

Luciferase activity of the above reporter vector was measured in the same manner as in Example 2 (1). The pGL4-miR140-3k vector prepared in Example 1 was also measured at the same time.

(3) Results

Figure 3:
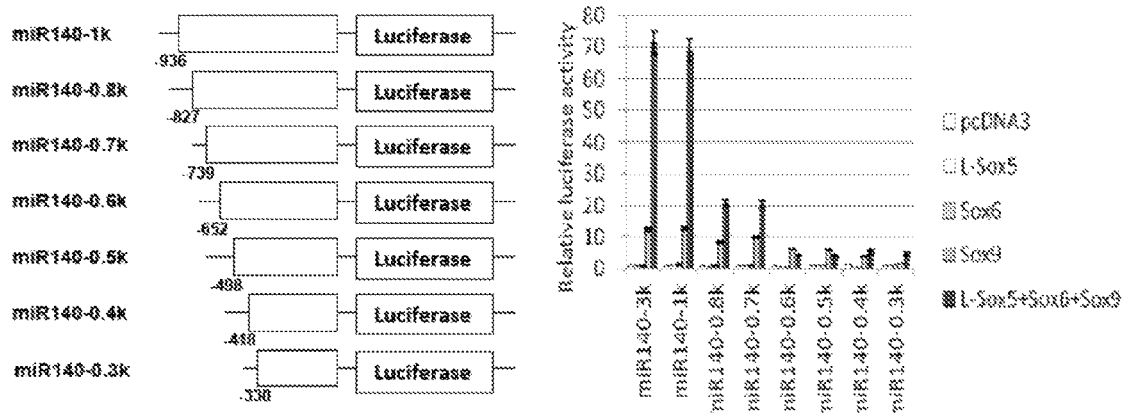
In FIG. 3, the left side shows the prepared reporter vectors and the right side is the result of evaluation of the luciferase activity of 293T cell transfected using them.

Results of this Example are shown in FIG. 3 (the graph in right side). pGL4-miR140-1k had the same luciferase activity as that of pGL4-miR140-3k. In pGL4-miR140-0.8k and pGL4-miR140-0.7k, the luciferase activity of the cell into which L-Sox5, Sox6 and Sox9 were transfected lowered as compared with that of pGL4-mi-R140-3k while the luciferase activity of the cell into which only Sox9 was transfected was similar to that of pGL-miR140-3k. With regard to the luciferase activity of pGL4-miR140-0.6k, pGL4-miR140-0.5k, pGL4-miR140-0.4k and pGL4-miR140-0.3k, it significantly lowered in both of the cell into which L-Sox5, Sox6 and Sox9 were transfected and the cell into which only Sox9 was transfected. In view of the above result, it was found that the DNA fragments having the sequence of any of SEQ ID Nos. 7 to 10 having the activity in this Example, the reporter vectors into which the DNA fragment was incorporated and the cells into which the reporter vector was introduced are useful for evaluating the action to the expression regulation of miR-140 by a combination of Sox9 expression vector, L-Sox5 expression vector and Sox6 expression vector. Further, it was suggested that the DNA sequence (SEQ ID No. 5) from −936 to −652 bp upstream region from the transcription start site of miR-140 is an essential region for the regulation of miR-140 expression by L-Sox5, Sox6 and Sox9 and that the essential region for the regulation thereby exists particularly in the sequence (SEQ ID No. 3) between −739 and −652 bp. Therefore, the sequence from −739 to −652 bp was precisely investigated and a palindromic Sox9 binding sequence was found (the uppermost line in frame of FIG. 4; SEQ ID No. 1).

Example 4

Figure 4:
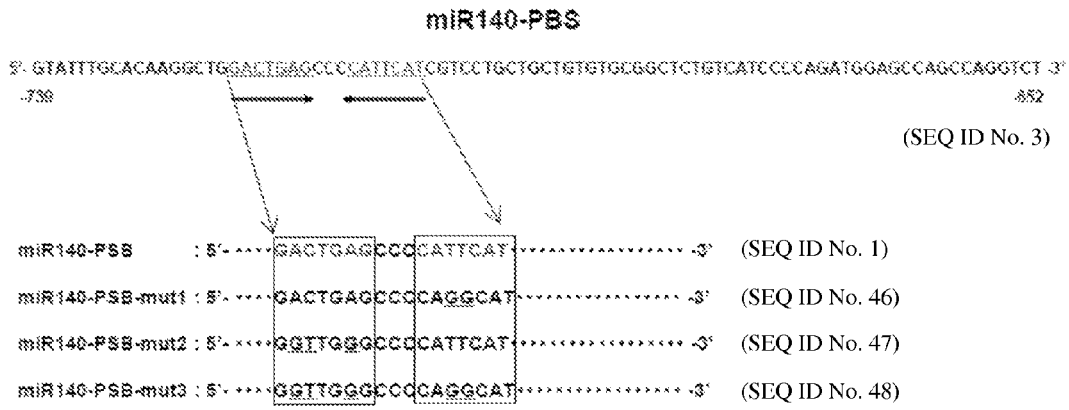
FIG. 4 shows the predicted palindromic Sox9 binding sequence and the mutations introduced thereinto.
Figure 5:
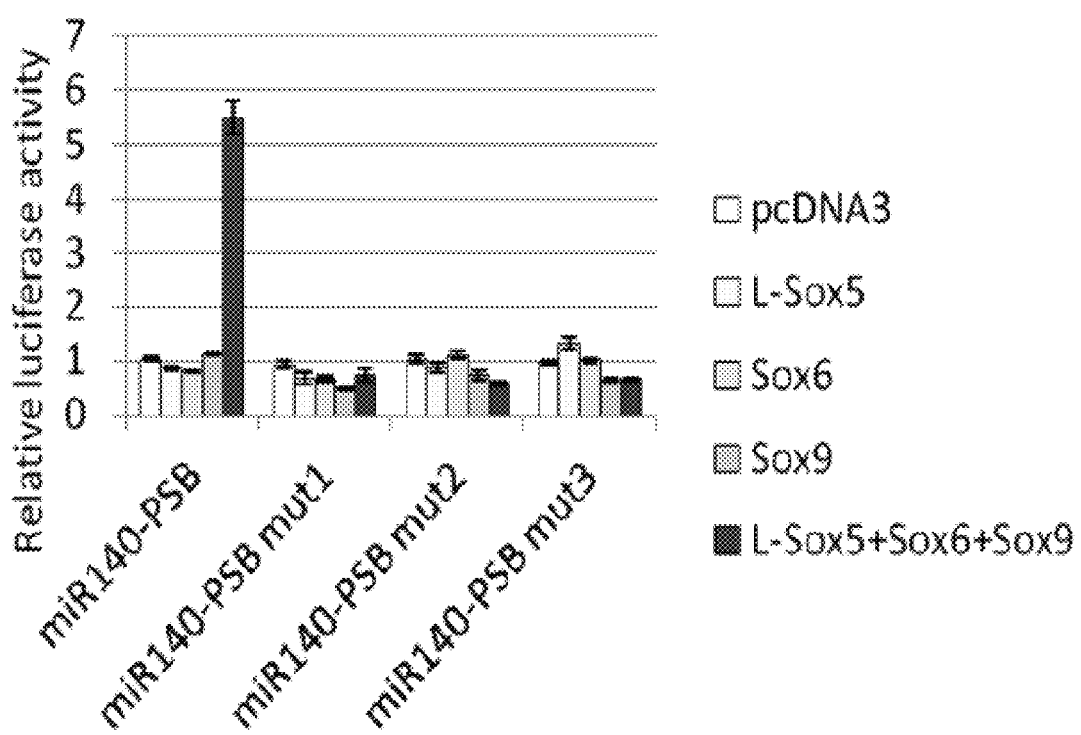
FIG. 5 is the result of evaluation of the luciferase activity of a palindromic Sox9 binding sequence or a mutation-introduced reporter vector.

Expression Regulation of miR-140 by Sox-Binding Region (1) Preparation of pGL4-miR140-PSB A forward primer containing XhoI cleavage site (GAACTCGAGGTATTTGCACAAGGCTGGAC) (SEQ ID No. 15) and a reverse primer containing BglII cleavage site (GCAAGATCTAGACCTGGCTGGCTGCAT) (SEQ ID No. 21) and pGL4-miR140-0.7k as a template were used and treated in the same manner as in Example 3(1) to give a reporter vector pGL4-miR140-PSB of FIG. 4 (upper line).

(2) Site-Directed Mutagenesis Method

A reporter plasmid where a mutation was introduced into the above Sox9 bound sequence was prepared by a site-directed mutagenesis method. Thus, in a reaction solution containing 1×PCR buffer, 0.2 mmol/L of dNTP, 1 U of Native Pfu DNA polymerase and each combination of primer of Table 2, using 20 ng of pG14-miR140-PSB in the case of production of miR140-PSB-mut1 and mut2 or using 20 ng of pGL4-miR140-PSB-mut1 in the case of production of mut3 as a template, the PCR was carried out under the condition of at 95° C. for 2 minutes and then of 18 cycles each comprising 95° C. for 30 seconds, 50° C. for 1 minute and 68° C. for 10 minutes. DnpI was added to the PCR product followed by subjecting to a restriction enzyme treatment at 37° C. for 1 hour. Similarly, a pGL4.12 luc2CP vector was subjected to a restriction enzyme treatment. The amplified DNA fragment was ligated with a pGL4.12 luc2CP vector by using ligation mix (manufactured by Takara Bio Inc.) and *Escherichia coli* made into competent cells was transformed to clone the vector into which the DNA fragment was incorporated. *Escherichia coli* after the cloning was incubated to purify a plasmid DNA whereupon a reporter vector of Table 2 and FIG. 4 (upper line) was prepared.

TABLE 2

| Reporter Vector | Primer | SEQ ID No. |
|---|---|---|
| pGL4-miR140-PSB-mut1 | CTGGACTGAGCCCCAGGCATCGTCCTGCTGCT | 22 |
| | AGCAGCAGGACGATGCCTGGGGCTCAGTCCAG | 23 |
| pGL4-miR140-PSB-mut2 | GTATTTGCACAAGGCTGGGTTGGGCCCCATTC ATCGTCCTG | 24 |
| | CAGGACGATGAATGGGGCCCAACCCAGCCTTG TGCAAATAC | 25 |
| pGL4-miR140-PSB-mut3 | ATTTGCACAAGGCTGGGTTGGGCCCCAGGCAT CGTCC | 26 |
| | GGACGATGCCTGGGGCCCAACCCAGCCTTGTG CAAAT | 27 |

(3) Reporter Assay

Luciferase activity of the above reporter vector was measured in the same manner as in Example 1(2).

(4) Results

Results of this Example are shown in FIG. 4. In the cell into which the reporter vector miR140-PSB (SEQ ID No. 3) containing the Sox9-binding sequence was introduced, the luciferase activity increased by the transfection of L-Sox5, Sox6 and Sox9 while, in miR140-PSB-mut1, miR140-PSB-mut2 and miR140-PSB-mut3 which were reporter plasmids where a mutation was introduced into the Sox9-binding sequence, no increase in luciferase activity was noted even by the transfection of L-Sox5, Sox6 and Sox9. Accordingly, it was clearly shown that the above Sox9-binding sequence is essential for the regulation of miR-140 expression by Sox. In addition, it was also found that the DNA fragment having the sequence of miR140-PSB (SEQ ID No. 3), the reporter vectors into which the DNA fragment was incorporated and the cells into which the reporter vector was introduced which were obtained in this Example were useful for evaluating the action to the expression regulation of miR-140 by the Sox9-expression vector.

Example 5

Sox9 Binding Activity of Sox Binding Sequence (1) Preparation of Probe

Sense oligo and antisense oligo having the sequences as shown in Table 3 were synthesized. To a reaction solution comprising 1× Protruding End Kinase buffer, 0.4 μmol/L of sense oligo or antisense oligo and 1 U of T4 Polynucleotide Kinase (manufactured by Toyobo Co., Ltd.) was added $P^{32}$ γATP followed by subjecting to a reaction at 37° C. for 1 hour. The sense oligo and the antisense oligo finishing each of their reactions were mixed, incubated at 99° C. for 10 seconds and gradually returned to room temperature during 1 hour to prepare a double-stranded DNA labeled with radioisotope (RI). The RI-labeled probe was used after purifying by PrbeQuant G-50 Micro Column.

TABLE 3

| Prove | Synthetic Oligo DNA | | SEQ ID No. |
|---|---|---|---|
| miR140-PSB | sense | CTGGACTGAGCCCCATTCATCG TCCTGCTGCT | 28 |
| | antisense | AGCAGCAGGACGATGAATGGGG CTCAGTCCAG | 29 |

TABLE 3 -continued

| Prove | | Synthetic Oligo DNA | SEQ ID No. |
|---|---|---|---|
| miR140-PSB-mut1 | sense | CTGGACTGAGCCCCAGGCATCG TCCTGCTGCT | 30 |
| | antisense | AGCAGCAGGACGATGCCTGGGG CTCAGTCCAG | 31 |
| miR140-PSB-mut2 | sense | CTGGGTTGGGCCCCATTCATCG TCCTGCTGCT | 32 |
| | antisense | AGCAGCAGGACGATGAATGGGG CCCAACCCAG | 33 |
| miR140-PSB-mut3 | sense | CTGGGTTGGGCCCCAGGCATCG TCCTGCTGCT | 34 |
| | antisense | AGCAGCAGGACGATGCCTGGGG CCCAACCCAG | 35 |

(2) Electrophoretic Mobility Shift Assay (EMSA)

To a reaction solution containing 20 mmol/L of HEPES (pH 7.9), 10% of glycerol, 50 mmol/L of KCl, 0.05% of NP-40, 0.5 mmol/L of EDTA, 0.5 mmol/L of DTT, 1 mmol/L of PMSF and 0.25 µg of Poly dG-dC was/were appropriately added 0.1 µg of a recombinant Sox9 (rSox9) and/or an anti-Sox9 antibody (manufactured by Millipore Corporation) followed by incubating at room temperature for 30 minutes. After that, the above RI-labeled probe was added, incubated at room temperature for 30 minutes and subjected to 4% polyacrylamide gel electrophoresis. After the electrophoresis, RI was detected using FLA-7000 (manufactured by Fujifilm) which is an image analysis apparatus.

(3) Results

Figure 6:
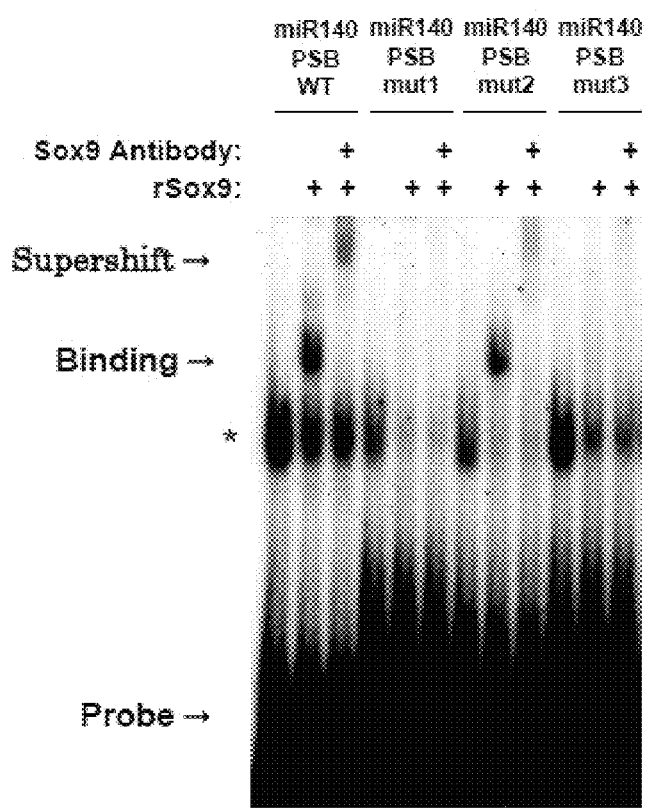
FIG. 6 is the result of evaluation of the Sox9 binding activity of a palindromic Sox9 binding consensus sequence and probes which a mutation is introduced thereinto.

Results of this Example are shown in FIG. 6. In miR-140-PSB probe, shift of the band was observed upon incubation with rSox9 and, upon further incubation with anti-Sox9 antibody, supershift of the band was observed. When miR-140-PSB-mut2 whose a mutation was introduced into the left side of the palindromic Sox9 binding sequence was used as a probe, shift of the band was observed but, when miR-140-PSB-mut1 or miR-140-PSB-mut3 whose a mutation was introduced into the right side or both sides was used as a probe, shift of the band disappeared. In view of the above results, it was made clear that the palindromic Sox9 binding sequence of SEQ ID No. 1 was essential for binding the Sox9 thereto. It was also found that the DNA having the sequence of SEQ ID No. 1 was useful as a probe for evaluating the binding activity to Sox9.

Example 5

Comparison of Sequences of Mice and Human in an Expression Regulatory Region of miR-140

Result of comparison of a DNA sequence of mice (SEQ ID No. 5) with a human homologous sequence (SEQ ID No. 6) is shown in FIG. 7. The sequences were compared by means of EMBOSS needle, which is a software for comparing the sequences provided by The European Molecular Biology Open Software Suite. Homology between both sequences was 71.5% (236 bases in 330 were identical). In the above, 16 bases (94.1%) in 17 were identical in the Sox binding sequence (in a frame of FIG. 7; SEQ ID Nos. 1 and 2) identified in the present invention. Further, homology of the 87 bp region of the above miR140-PSB (SEQ ID No. 3) with human homologous sequence (SEQ ID No. 4) was 72.2% (65 bases in 90 were identical). Accordingly, the DNA fragment of human homologous sequence of miR-140 expression regulation region being made clear in this Example, the reporter vector into which the DNA fragment is incorporated and the cell into which the reporter vector is introduced are useful for evaluating the action of a drug to the expression regulation of miR-140.

Example 6

Expression Regulation of miR-140 in Transgenic Mice (1) Preparation of Reporter Plasmid PCR was carried out using a forward primer containing HindIII cleavage site (CCAAGCTTGGCCGCAGACCGT-GCATCATGA) (SEQ ID No. 36) and a reverse primer containing NcoI cleavage site (CATGCCATGGCATGCA-GCTTGGGCCCTCGAG) (SEQ ID No. 37) and 10 ng of pAxCAiLacZ (manufactured by Takara Bio Inc.) as a template. Thus, PrimeStar HS DNA polymerase (manufactured by Takara Bio Inc.) was used and a solution containing 1×PCR reaction solution, 0.2 mmol/L of dNTP, 0.2 µmol/L of each primer, 0.5 U of PrimeStar HS DNA polymerase and 10 ng of genomic DNA was subjected to PCR under the condition of at 98° C. for 2 minutes, then of 25 cycles each comprising 98° C. for 10 seconds, 60° C. for 15 seconds and 72° C. for 4 minutes and of at 72° C. for 5 minutes to amplify the DNA fragment of LacZ. The DNA fragments were subjected to a restriction enzyme treatment in 1×M buffer by HindIII and NcoI which are restriction enzymes. pGL4.12 luc2CP was similarly subjected to a restriction enzyme treatment. The amplified DNA fragments were ligated with a pGL4.12 luc2CP vector using a ligation mix (manufacture by Takara Bio Inc.) and *Escherichia coli* made in competent cells was transformed to clone the vector into which the DNA fragment was incorporated. *Escherichia coli* after the cloning was incubated to prepare a plasmid DNA whereupon a reporter vector pGL4-LacZ was obtained.

pGL4-miR140-3k was subjected to an enzymatic treatment with NotI and XhoI and the aimed DNA fragment containing miR-140-3k was purified using a MinElute Gel Extraction kit. pcDNA was treated in the same manner as well. The amplified DNA fragments were ligated with a pcDNA3 vector using a ligation mix and *Escherichia coli* made into competent cells was transformed to clone the vector into which the DNA fragment was incorporated. *Escherichia coli* after the cloning was incubated to prepare a plasmid DNA and the vector where the aimed DNA fragment was cloned was obtained. The resulting vector was subjected to a restriction enzyme treatment using KpnI and XbaI and the aimed DNA fragment was purified by MinElute Gel Extraction kit. pGL4-LacZ was subjected to a restriction enzyme treatment with KpnI and NheI and purified by MinElute Gel Extraction kit. The amplified DNA fragment was ligated with a pGL4-LacZ vector using a ligation mix and transformed to *Escherichia coli* made into competent cells was transformed to clone the vector into which the DNA fragment was incorporated. *Escherichia coli* after the cloning was incubated to purify a plasmid DNA and a reporter vector pGL4-miR140-3k-LacZ was obtained.

(2) Preparation of Transgenic Mice

Figure 8:
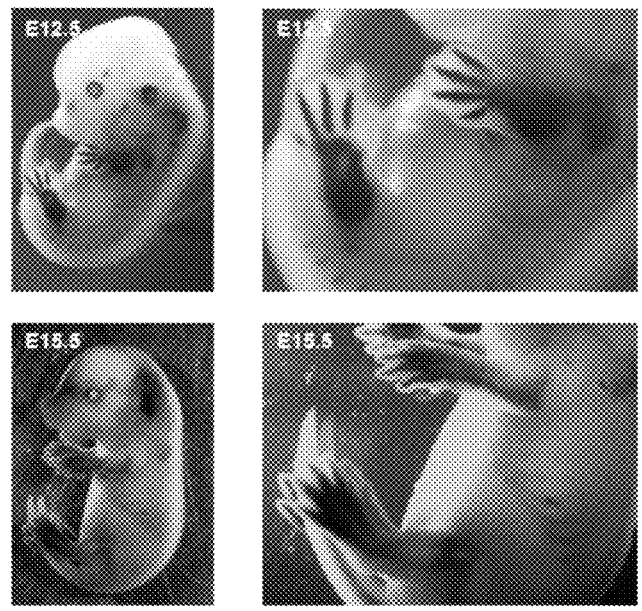
FIG. 8 is the result of evaluation of expression of LacZ in a transgenic mouse into which pGL4-miR140-LacZ is introduced.

The resulting reporter vector was subjected to a restriction enzyme treatment using KpnI and NcoI to prepare a DNA fragment of miR140-3k-LacZ (upper line of FIG. 8). The DNA fragment was introduced into a fertilized egg pronuclear and transgenic mice were prepared.

(3) Staining In Situ

Genomic DNA was obtained from amnions of the transgenic mice and subjected to PCR using a forward primer (GGTGCTTTGTGAAGGGAAAG) (SEQ ID No. 38) and a reverse primer (GTTGCACCACAGATGAAACG) (SEQ ID No. 39) to select individuals having the reporter vector. Thus, a reaction solution containing 1× Green GoTaq Flexi buffer, 0.25 mmol/L of $MgCl_2$, 0.16 mmol/L of dNTP, 0.2 mmol/L of each primer and 0.6 U of GoTaq Hot Start Polymerase was prepared and PCR was carried out. Selected individuals were fixed at 4° C. for 30 minutes in a phosphate buffered saline (PBS) containing 1% of paraformaldehyde, 0.2% of glutaraldehyde and 0.02% of NH-40. After the above was washed with PBS containing 1 mmol/L of $MgCl_2$, it was dipped in PBS containing 0.01% of sodium deoxycholate, 0.02% of NP-40, 1 mol/L of $MgCl_2$, 5 mmol/L of $K_4Fe(CN)_6$, 5 mmol/L of $K_3Fe(CN)_6$ and 0.1% of X-Gal and stained by means of incubation at 37° C. for 16 hours.

(4) Results

Results of this Example are shown in FIG. 8. In the fetus of E 12.5 days age and E 15.5 days age, it was made clear that forelimbs, hind limbs and other cartilage tissues such as rims and vertebrae were stained by means of X-gal staining showing the LacZ activity and that these regions were an expression regulation region for miR-140 which is cartilage-specifically expressed. Thus, the transgenic mice prepared in this Example are useful for evaluating the activity of a drug that regulates the expression of miR-140.

Example 7

Confirmation of Function of Human miR-140 Expression Regulatory Region (1) Preparation of Reporter Vector A forward primer containing HindIII cleavage site (CCCAGCTTGGGACTCCAAATTGCATTATCGA-GAAAC) (SEQ ID No. 42) and a reverse primer containing NcoI cleavage site (CATGCCATGGCATGAGTGCCTC-CGCTCAGCTCCG) (SEQ ID No. 43) were used and PCR was carried out using genomic DNA of incubated human chondrocytes as a template so as to amplify the DNA fragment (SEQ ID No. 40) in 3 kbp upstream region from the human miR-140 transcription starting site. Thus, a reaction solution containing 1×PCR reaction solution, 0.2 mmol/L of dNTP, 0.2 µmol/L of each primer, 0.5 U of PrimeStar HS DNA polymerase and 10 ng of genomic DNA was prepared, heated at 98° C. for 2 minutes, subjected 35 cycles each comprising 98° C. for 10 seconds, 60° C. for 5 seconds and 72° C. for 3 minutes, and then subjected to a treatment at 72° C. for 7 minutes to conduct the PCR. The amplified DNA fragments were subjected to a restriction enzyme treatment in 1×M buffer using HindIII and NcoI. pGL4.12 luc2CP having luciferase gene as a reporter was similarly subjected to a restriction enzyme treatment. The amplified DNA fragment was ligated with a pGL4.12 luc2CP vector using a ligation mix and *Escherichia coli* made into competent cells was transformed to clone the vector into which the DNA fragment was incorporated. *Escherichia coli* after the cloning was incubated to purify the plasmid DNA whereupon a reporter vector pGL4-hgmiR140-3k was obtained.

In addition, a forward primer containing HindIII cleavage site (CCCAAGCTTGGGGTTTTCTCAAGCCGACACT-GAGC (SEQ ID No. 44) and a reverse primer containing NcoI cleavage site (CATGCCATGGCATGAGTGCCTC-CGCTCAGCTCCG (SEQ ID No. 45) were used to conduct PCR using pGL4-hgmiR140-3k as a template whereby the DNA fragment (SEQ ID No. 41) in 0.7 kbp upstream region from the human miR-140 transcription starting site were amplified. Thus, a reaction solution containing 1×PCR reaction solution, 0.2 mmol/L of dNTP, 0.2 µmol/L of each primer, 0.5 U of PrimeStar HS DNA polymerase and 10 ng of genomic DNA was prepared, heated at 98° C. for 2 minutes, subjected 30 cycles each comprising 98° C. for 10 seconds, 60° C. for 5 seconds and 72° C. for 1 minute, and subjected to a treatment at 72° C. for 7 minutes to carry out the PCR. The amplified DNA fragment was similarly cloned to give a reporter vector pGL4-hgmiR140-0.7k.

(2) Measurement of Reporter Activity

Luciferase activity of the above reporter vector was measured in the same manner as in Example 2(1).

(3) Results

Figure 9:
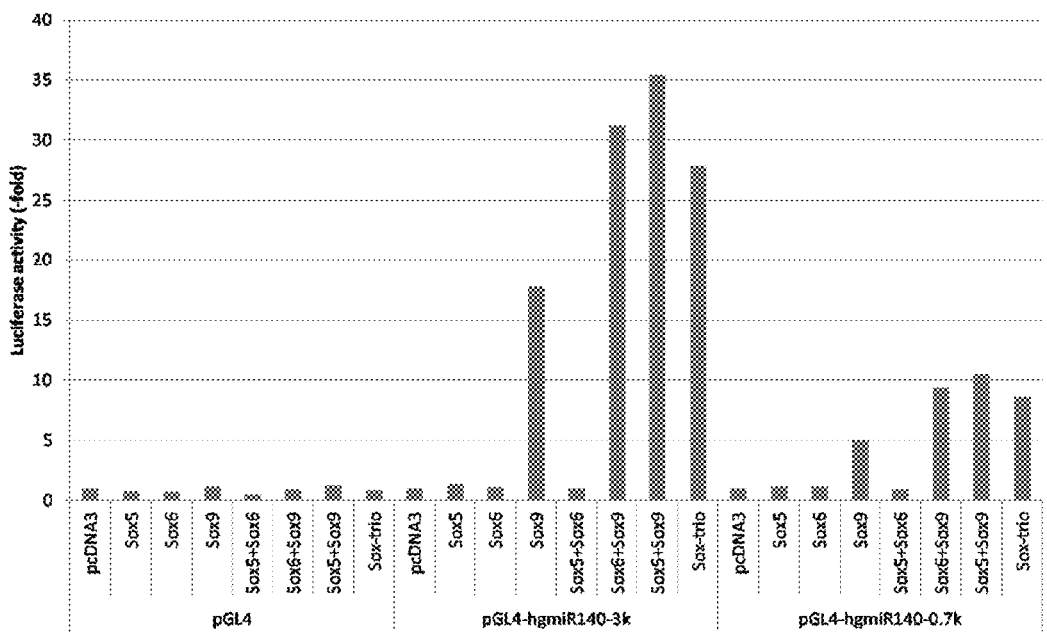
FIG. 9 is the result of evaluation of influence of a combination of co-transfected L-Sox5, Sox6 and/or Sox9 expression vector(s) on the luciferase activity of 293T cell into which pGL4, pGL4-hgmiR140-3k or pGL4-hgmiR140-0.7k is transfected.

Results of this Example are shown in FIG. 9. Even in the case of cells into which pGL4-hgmiR140-0.7k or pGL4-hgmiR140-3k containing human homologous sequence being made clear in Example 5, which is a reporter vector where upstream region of human pri-miR-140 transcription starting site is cloned, was introduced, the luciferase activity increased by the transfection of Sox9, as in the case of pGL4-miR140-0.7k or pGL4-miR140-3k of Example 3 prepared by cloning of upstream region of pri-miR-140 transcription starting site of the mice corresponding thereto and, when L-Sox5 and/or Sox6 were/was further transfected, the luciferase activity was much more potentiated. In view of the above results, it was shown that the human homologous sequence which was made clear in Example 5 functioned as a human miR-140 expression regulatory region and it was found that the gene fragment having the sequence of SEQ ID No. 40 or 41, the reporter vector into which the DNA was incorporated and the cell into which the reporter vector was introduced were useful for evaluating the action of a drug to the expression regulation of human miR-140.

INDUSTRIAL APPLICABILITY

In accordance with the present invention, there are provided a DNA having the activity of regulating the expression of miR-140, a reporter vector containing the DNA, cells and animals into which the reporter vector is introduced, a screening system for a drug regulating the expression of miR-140, etc. The DNA sequence is able to express any gene in a site where miR-140 is expressed and, in addition, it is also able to utilize for screening a drug which regulates the expression of miR-140. Moreover, a drug which is selected by the screening system is expected as a treating agent for cartilage diseases such as osteoarthritis, intervertebral disk degeneration, etc. accompanied with abnormality of cartilage and, consequently, the present invention is very highly useful in industry.

The invention claimed is:

1. A vector comprising:
 a first DNA sequence that includes at least one of:
  the nucleotide sequence of SEQ ID No. 1 or 2; and
 a reporter gene downstream of the first DNA sequence.

2. The vector according to claim 1, wherein the reporter gene is LacZ, β-glucosidase, β-glucuronidase, alkaline phosphatase, chloramphenicol acetyl transferase (CAT), luciferase or fluorescent protein.

3. An isolated cell into which the vector of claim 1 is introduced.

4. The isolated cell according to claim 3, wherein the cell is any cell selected from the group consisting of a 293T cell, ATDC5 cell, SW1353 cell, primarily cultured chondrocyte, mesenchymal stem cell and embryonic stem cell (ES cell).

5. A non-human animal into which the vector of claim 1 is introduced.

6. The non-human animal according to claim 5, wherein the animal is a mouse or a rat.

7. A method for screening a drug which regulates the expression of miR-140, comprising
 detecting reporter activity in the cell of claim 3 in the presence of a drug; and
 comparing the detected reporter activity with a control reporter activity detected in the absence of a drug to determine if the drug increases or decreases the reporter activity.

8. A method for screening a drug which regulates the expression of miR-140, the method comprising:
 (a) contacting a drug with the cell of claim 3;
 (b) detecting a reporter activity in the cell; and
 (c) selecting a drug which increases or decreases the reporter activity by comparing with a control detected in the absence of a drug.

9. A method for screening a drug which regulates the expression of miR-140, the method comprising:
 introducing the vector of claim 1 into a cell;
 contacting a drug with the cell;
 detecting a reporter activity in the cell; and
 selecting a drug that increases or decreases the reporter activity by comparing with a control detected in the absence of a drug.

10. The vector according to claim 1, wherein the nucleotide sequence of SEQ ID No. 1 or 2 is repeated in the vector from two to five times.

11. The vector according to claim 1, wherein the first DNA sequence further includes a nucleotide sequence having at least 60% sequence identity with the nucleotide sequence of SEQ ID No. 3 or 4.

12. The vector according to claim 1, wherein the first DNA sequence further includes a nucleotide sequence having at least 60% sequence identity with the nucleotide sequence of SEQ ID No. 5 or 6.

13. The vector according to claim 1, wherein the first DNA sequence further includes a nucleotide sequence having at least 60% sequence identity with any of the nucleotide sequences selected form the group consisting of SEQ ID Nos. 7-10, 40, and 41.

14. The vector according to claim 11, wherein the nucleotide sequence of the first DNA sequence includes the nucleotide sequence of SEQ ID No. 1 or 2 and has at least 70% sequence identity with the nucleotide sequence of SEQ ID No. 3 or 4.

15. The vector according to claim 12, wherein the nucleotide sequence of the first DNA sequence includes the nucleotide sequence of SEQ ID No. 1 or 2 and has at least 70% sequence identity with the nucleotide sequence of SEQ ID No. 5 or 6.

16. The vector according to claim 13, wherein the nucleotide sequence of the first DNA sequence includes the nucleotide sequence of SEQ ID No. 1 or 2 and has at least 70% sequence identity with any of the nucleotide sequences selected form the group consisting of SEQ ID Nos. 7-10, 40, and 41.

17. A method of detecting reporter activity, comprising:
 introducing the vector of claim 1 into a cell; and
 detecting reporter activity in the cell.

* * * * *

SEQUENCE LISTING

<160> NUMBER OF SEQ ID NOS: 48

<210> SEQ ID NO 1
<211> LENGTH: 17
<212> TYPE: DNA
<213> ORGANISM: Mus musculus

<400> SEQUENCE: 1
gactgagccc cattcat                                                        17

<210> SEQ ID NO 2
<211> LENGTH: 17
<212> TYPE: DNA
<213> ORGANISM: Homo sapiens

<400> SEQUENCE: 2
cactgagccc cattcat                                                        17

<210> SEQ ID NO 3
<211> LENGTH: 87
<212> TYPE: DNA
<213> ORGANISM: Mus musculus

<400> SEQUENCE: 3
gtatttgcac aaggctggac tgagccccat tcatcgtcct gctgctgtgt gcggctctgt         60
catccccaga tggagccagc caggtct                                             87

<210> SEQ ID NO 4
<211> LENGTH: 85
<212> TYPE: DNA
<213> ORGANISM: Homo sapiens

<400> SEQUENCE: 4
ttttctcaag ccgacactga gccccattca tcctcctgcc catgtgtggc tccggcaccc         60
ctagacgggg ccagcccagc agcct                                               85

<210> SEQ ID NO 5
<211> LENGTH: 284
<212> TYPE: DNA
<213> ORGANISM: Mus musculus

<400> SEQUENCE: 5
cagctcctcc aacttttcag gcttcctttg tgaaaggggc cctatcccat caaggaacct         60
atggtttcaa gacttactgt tggaattact tggaagagga gcctgtgttg ccaccttggg        120
aagaaagttt ctctgtccct tcagttgggg gtagcgggag ggctgcagtg ggcttggctg        180
gcagtggagc accactggta tttgcacaag gctggactga gccccattca tcgtcctgct        240
gctgtgtgcg gctctgtcat ccccagatgg agccagccag gtct                         284

<210> SEQ ID NO 6
<211> LENGTH: 319
<212> TYPE: DNA
<213> ORGANISM: Homo sapiens

<400> SEQUENCE: 6
gagcttcccc cacctccgtg cacttgcatt ctgtgtgggc aggaggccct gccctgaaag         60
ggggctccgt cctgtcaaga gcctatggtt tcaagactta acatctttg ttggaacttg        120 cttggaagag gggcctgtgt tgccaccttg gaaagaaagt ttctctgtcc tttcagctgg        180
gggtggaggg agggctgtgg aaggggcgtt gctggcagtt gagttccacc aatgtttct        240

```
caagccgaca ctgagcccca ttcatcctcc tgcccatgtg tggctccggc accccctagac    300 ggggccagcc cagcagcct                                                  319

<210> SEQ ID NO 7
<211> LENGTH: 739
<212> TYPE: DNA
<213> ORGANISM: Mus musculus

<400> SEQUENCE: 7
gtatttgcac aaggctggac tgagccccat tcatcgtcct gctgctgtgt gcggctctgt     60 catcccccaga tggagccagc caggtctgca gcctgaagtc tgcattcaga acttgatccc   120
ctaatacgat gattaaattc tagtaagtga aataaaaatg cttgagtggg ggagagaacg    180
gagtcaaata atcgtcgttt tatttaacta tgaaaagttt ttgacatgcg ccctctgcat    240
cccgaaggct acgaggactc tctctccatc tattgcagcc cttcccctgg gaccttgagg    300
caataatagg ccgaagggc agtgtaaatg gtgaccctga cggcccaaag ccccttcccc     360 cttcccttc accagcccca gcaccaactc cccagacagg caaacacaga acactgagca     420
acttgaggtt caggcaggga agaataaagg tgctttgtga agggaaagga aaacattct     480 gggggaggtg agggggcttgg gcatgaaagt gccctcagtc tgggtggatg ctgcacaccc   540
aggagggagg tggtgggagg agggccgggc cccagccagg aagccctggg cgtgggcagg    600
gcttgtggga atgatttcat tggaaaggcc tgcggtattt ttcccctcc tgtgtgtggt     660 tcttggagaa agttggaggt ggtgaggatt tcagttgcct tggccgccgg gcgggagcag    720
gagctgagca gaggtcggt                                                 739

<210> SEQ ID NO 8
<211> LENGTH: 827
<212> TYPE: DNA
<213> ORGANISM: Mus musculus

<400> SEQUENCE: 8
gccaccttgg gaagaaagtt tctctgtccc ttcagttggg ggtagcggga gggctgcagt     60
gggcttggct ggcagtggag caccactggt atttgcacaa ggctggactg agccccattc    120
atcgtcctgc tgctgtgtgc ggctctgtca tccccagatg gagccagcca ggtctgcagc    180
ctgaagtctg cattcagaac ttgatcccct aatacgatga ttaaattcta gtaagtgaaa    240
taaaaatgct tgagtggggg agagaacgga gtcaaataat cgtcgtttta tttaactatg    300
aaaagttttt gacatgcgcc ctctgcatcc cgaaggctac gaggactctc tctccatcta    360
ttgcagccct tcccctggga ccttgaggca ataataggcc gaaggggcag tgtaaatggt    420
gaccctgacg gcccaaagcc ccttcccct tccctttcac cagccccagc accaactccc     480
cagacaggca aacacagaac actgagcaac ttgaggttca ggcagggaag aataaaggtg    540
ctttgtgaag ggaaaggaaa acatttctgg gggaggtgag gggcttgggc atgaaagtgc    600
cctcagtctg ggtggatgct gcacacccag gagggaggtg gtgggaggag ggccgggccc    660
cagccaggaa gccctgggcg tgggcagggc ttgtgggaat gatttcattg gaaaggcctg    720
cggtattttt tcccctcctg tgtgtggttc ttggagaaag ttggaggtgg tgaggatttc    780
agttgccttg gccgccgggc gggagcagga gctgagcaga ggtcggt                  827

<210> SEQ ID NO 9
<211> LENGTH: 936
<212> TYPE: DNA
```

<213> ORGANISM: Mus musculus

<400> SEQUENCE: 9

| | | | | | |
|---|---|---|---|---|---|
| cagctcctcc | aacttttcag | gcttcctttg | tgaaaggggc | cctatcccat | caaggaacct | 60 |
| atggtttcaa | gacttactgt | tggaattact | tggaagagga | gcctgtgttg | ccaccttggg | 120 |
| aagaaagttt | ctctgtccct | tcagttgggg | gtagcgggag | ggctgcagtg | ggcttggctg | 180 |
| gcagtggagc | accactggta | tttgcacaag | gctggactga | gccccattca | tcgtcctgct | 240 |
| gctgtgtgcg | gctctgtcat | ccccagatgg | agccagccag | gtctgcagcc | tgaagtctgc | 300 |
| attcagaact | tgatccccta | atacgatgat | taaattctag | taagtgaaat | aaaaatgctt | 360 |
| gagtggggga | gagaacggag | tcaaataatc | gtcgttttat | ttaactatga | aaagttttttg | 420 |
| acatgcgccc | tctgcatccc | gaaggctacg | aggactctct | ctccatctat | tgcagccctt | 480 |
| cccctgggac | cttgaggcaa | taataggccg | aaggggcagt | gtaaatggtg | accctgacgg | 540 |
| cccaaagccc | cttcccccctt | ccctttcacc | agccccagca | ccaactcccc | agacaggcaa | 600 |
| acacagaaca | ctgagcaact | tgaggttcag | gcagggaaga | ataaaggtgc | tttgtgaagg | 660 |
| gaaaggaaaa | catttctggg | ggaggtgagg | ggcttgggca | tgaaagtgcc | ctcagtctgg | 720 |
| gtggatgctg | cacacccagg | agggaggtgg | tgggaggagg | gccgggcccc | agccaggaag | 780 |
| ccctgggcgt | gggcagggct | tgtgggaatg | atttcattgg | aaaggcctgc | ggtatttttt | 840 |
| cccctcctgt | gtgtggttct | tggagaaagt | tggaggtggt | gaggatttca | gttgccttgg | 900 |
| ccgccgggcg | ggagcaggag | ctgagcagag | gtcggt | | | 936 |

<210> SEQ ID NO 10
<211> LENGTH: 3012
<212> TYPE: DNA
<213> ORGANISM: Mus musculus

<400> SEQUENCE: 10

| | | | | | |
|---|---|---|---|---|---|
| actgttcaga | aggagactac | tctgtccctc | cctcagccct | ccgaccacat | cctcagacac | 60 |
| ctggagcttg | ctctggccca | tcaggtccac | cctgcaaaca | tgatgctgcc | ttcttctctg | 120 |
| aactctctga | ccttcccaga | gtctttcctg | cccttggctg | tgcttgctag | acattcttta | 180 |
| tttctgagtt | tgtatctcaa | aatattcctg | ggactctgtg | cttaatccca | gagggagttg | 240 |
| aactcacatg | agctttctgg | ctcacggcta | caccctgcgc | ctccagccct | ggatattccc | 300 |
| cagggaggtg | tctcagcagt | cacatttgtg | tttctgatta | tggaggacct | tgtttctcag | 360 |
| agttaacttg | catccaggag | ctcccttctg | gcatcagtca | gtcccttgt | cctgtccgtg | 420 |
| tgcctttcca | tctcttctct | gtagaacaca | cttgaaccct | cgggagatga | ggagaaggag | 480 |
| catttggttg | cccactgaag | gacttgcttg | gggttttctg | gccatgatgc | aaagctttta | 540 |
| tttattgttt | ttccctcact | tctgtgtctc | ttctcttctc | ttctcttctc | ttctcttctc | 600 |
| ttctcttctc | ttctcttctc | ttctcttctc | ttctcatggc | tggagagaca | gctgtgagtg | 660 |
| ctgggaactg | aactcttata | gttttttgttg | tgagcctagc | ctttaacagc | tgagccatct | 720 |
| ctccagccca | ccctttctttt | tcttatgatt | tgagttgtaa | aatgtacctg | aaaggaaaaa | 780 |
| ctaaccccaa | aaaagtcatg | tgatccactt | tagctgtaac | agtaaaatca | ccataggagt | 840 |
| ccaagggtcc | tgagtgcttc | tgttgggctc | ttcggtctcg | tccgtccctt | ccttccttct | 900 |
| gtctttcctc | tctggccttc | ctgcaggctg | agggtatgtg | tgatgagtgg | agctataggg | 960 |
| gaacaactgg | agggccactt | agtgaggag | agccaacgtc | atgatgtttg | ggatagaaac | 1020 |
| aacaaaacca | aactaaaaag | aacaaggcta | agcaaagggt | gttagctgag | cacagcgtcc | 1080 |

```
acacctggaa tcccacggtt gggaagttga gttaaggagc tcacatgagc ctgagtttga   1140
acccagcctg aactatatag agagatttca tttcaagaaa aaaagagact gatgaatagt   1200
ttggttccaa attctgtgcc atcagtaaca ttttgacctg gttgcagagt gaagtataag   1260
gtgaggagaa gctggctgag tccgtccctg ctaaaacctg gggtacttta tacattagct   1320
acacattcca aagagtctga agccagttgc ctcctctttt tctttctttg tcgttttctt   1380
ttgttgttgt tttgaggcag gttttctcta cataatctgg acagcctgga gcttgctatg   1440
tagaccaggc tatccttgag ctcacagaga cccattccaa gcgttgggct taaaggtgtg   1500
tgccaccaca cctggcttgt ttcagttgca ggctgggcat gtgctccgtg ataagagcat   1560
tcttaagcca ggtgtggtgg tttacgcctt taatcccagc acttgggagg cagaggcagg   1620
tggatttctg agttcgaggc cagcctggtc tacaaagtga gttccaggac agccagggct   1680
acacaaaaaa accctgtctc gaaaaaccaa aaaaaaaaaa aaaaaaaaaa gagcattctt   1740
atcagtgacc tagtatgtgt gagtccccag ggttcagttc ccgaaagctg cagtcatgcc   1800
tgtcgctcag tgctgaccac cgcctttggt ttgcctggta tctgatggat gcacgtgttt   1860
cctattcgtt cttcaacttt ctgctgctaa gtgctttcac gaaggctctt acacccttaa   1920
ctagcaagtg gagcaggggt cttctgaggt gctgagtctc accgacgccc gccctcccca   1980
tacctagaca cacccagcag cccagtgtga attgggcttc agtcctgagg cagatctgag   2040
ctgggatggc attggtaatg ggcatcaaac caaggccagc tcctccaact tttcaggctt   2100
cctttgtgaa aggggcccta tcccatcaag gaacctatgg tttcaagact tactgttgga   2160
attacttgga agaggagcct gtgttgccac cttgggaaga aagtttctct gtcccttcag   2220 ttggggggtag cggagggct gcagtgggct tggctggcag tggagcacca ctggtatttg   2280
cacaaggctg gactgagccc cattcatcgt cctgctgctg tgtgcggctc tgtcatcccc   2340
agatggagcc agccaggtct gcagcctgaa gtctgcattc agaacttgat ccctaatac   2400 gatgattaaa ttctagtaag tgaaataaaa atgcttgagt gggggagaga acggagtcaa   2460
ataatcgtcg ttttatttaa ctatgaaaag ttttttgacat gcgccctctg catcccgaag   2520
gctacgagga ctctctctcc atctattgca gcccttcccc tgggaccttg aggcaataat   2580
aggccgaagg ggcagtgtaa atggtgaccc tgacggccca agccccttc cccttccct   2640 ttcaccagcc ccagcaccaa ctccccagac aggcaaacac agaacactga gcaacttgag   2700
gttcaggcag ggaagaataa aggtgctttg tgaagggaaa ggaaaacatt tctgggggag   2760
gtgaggggct tggcatgaa agtgccctca gtctgggtgg atgctgcaca cccaggaggg   2820
aggtggtggg aggagggccg ggccccagcc aggaagccct gggcgtgggc agggcttgtg   2880
ggaatgattt cattggaaag gcctgcggta ttttttcccc tcctgtgtgt ggttcttgga   2940
gaaagttgga ggtggtgagg atttcagttg ccttggccgc cgggcgggag caggagctga   3000
gcagaggtcg gt                                                      3012
```

<210> SEQ ID NO 11
<211> LENGTH: 34
<212> TYPE: DNA
<213> ORGANISM: Artificial Sequence
<220> FEATURE:
<223> OTHER INFORMATION: Synthetic Construct

<400> SEQUENCE: 11

```
aaggtaccac tgttcagaag gagactactc tgtc                                34
```

<210> SEQ ID NO 12
<211> LENGTH: 28
<212> TYPE: DNA
<213> ORGANISM: Artificial Sequence
<220> FEATURE:
<223> OTHER INFORMATION: Synthetic Construct

<400> SEQUENCE: 12
gcactcgaga ccgacctctg ctcagctc                                            28

<210> SEQ ID NO 13
<211> LENGTH: 30
<212> TYPE: DNA
<213> ORGANISM: Artificial Sequence
<220> FEATURE:
<223> OTHER INFORMATION: Synthetic Construct

<400> SEQUENCE: 13
gaactcgagc agctcctcca acttttcagg                                          30

<210> SEQ ID NO 14
<211> LENGTH: 29
<212> TYPE: DNA
<213> ORGANISM: Artificial Sequence
<220> FEATURE:
<223> OTHER INFORMATION: Synthetic Construct

<400> SEQUENCE: 14
gaactcgagg ccaccttggg aagaaagtt                                           29

<210> SEQ ID NO 15
<211> LENGTH: 29
<212> TYPE: DNA
<213> ORGANISM: Artificial Sequence
<220> FEATURE:
<223> OTHER INFORMATION: Synthetic Construct

<400> SEQUENCE: 15
gaactcgagg tatttgcaca aggctggac                                           29

<210> SEQ ID NO 16
<211> LENGTH: 29
<212> TYPE: DNA
<213> ORGANISM: Artificial Sequence
<220> FEATURE:
<223> OTHER INFORMATION: Synthetic Construct

<400> SEQUENCE: 16
gaactcgagg cagcctgaag tctgcattc                                           29

<210> SEQ ID NO 17
<211> LENGTH: 29
<212> TYPE: DNA
<213> ORGANISM: Artificial Sequence
<220> FEATURE:
<223> OTHER INFORMATION: Synthetic Construct

<400> SEQUENCE: 17
gaactcgagc cgaaggctac gaggactct                                           29

<210> SEQ ID NO 18
<211> LENGTH: 30
<212> TYPE: DNA
<213> ORGANISM: Artificial Sequence
<220> FEATURE:
<223> OTHER INFORMATION: Synthetic Construct

<400> SEQUENCE: 18
gaactcgagg tgtaaatggt gaccctgacg                                30

<210> SEQ ID NO 19
<211> LENGTH: 28
<212> TYPE: DNA
<213> ORGANISM: Artificial Sequence
<220> FEATURE:
<223> OTHER INFORMATION: Synthetic Construct

<400> SEQUENCE: 19
gaactcgaga acactgagca acttgagg                                  28

<210> SEQ ID NO 20
<211> LENGTH: 28
<212> TYPE: DNA
<213> ORGANISM: Artificial Sequence
<220> FEATURE:
<223> OTHER INFORMATION: Synthetic Construct

<400> SEQUENCE: 20
gcaagatcta ccgacctctg ctcagctc                                  28

<210> SEQ ID NO 21
<211> LENGTH: 27
<212> TYPE: DNA
<213> ORGANISM: Artificial Sequence
<220> FEATURE:
<223> OTHER INFORMATION: Synthetic Construct

<400> SEQUENCE: 21
gcaagatcta gacctggctg gctccat                                   27

<210> SEQ ID NO 22
<211> LENGTH: 32
<212> TYPE: DNA
<213> ORGANISM: Artificial Sequence
<220> FEATURE:
<223> OTHER INFORMATION: Synthetic Construct

<400> SEQUENCE: 22
ctggactgag ccccaggcat cgtcctgctg ct                             32

<210> SEQ ID NO 23
<211> LENGTH: 32
<212> TYPE: DNA
<213> ORGANISM: Artificial Sequence
<220> FEATURE:
<223> OTHER INFORMATION: Synthetic Construct

<400> SEQUENCE: 23
agcagcagga cgatgcctgg ggctcagtcc ag                             32

<210> SEQ ID NO 24
<211> LENGTH: 41
<212> TYPE: DNA
<213> ORGANISM: Artificial Sequence
<220> FEATURE:
<223> OTHER INFORMATION: Synthetic Construct

<400> SEQUENCE: 24
gtatttgcac aaggctgggt tgggccccat tcatcgtcct g                   41

<210> SEQ ID NO 25

<211> LENGTH: 41
<212> TYPE: DNA
<213> ORGANISM: Artificial Sequence
<220> FEATURE:
<223> OTHER INFORMATION: Synthetic Construct

<400> SEQUENCE: 25
caggacgatg aatggggccc aacccagcct tgtgcaaata c             41

<210> SEQ ID NO 26
<211> LENGTH: 37
<212> TYPE: DNA
<213> ORGANISM: Artificial Sequence
<220> FEATURE:
<223> OTHER INFORMATION: Synthetic Construct

<400> SEQUENCE: 26
atttgcacaa ggctgggttg ggccccaggc atcgtcc                  37

<210> SEQ ID NO 27
<211> LENGTH: 37
<212> TYPE: DNA
<213> ORGANISM: Artificial Sequence
<220> FEATURE:
<223> OTHER INFORMATION: Synthetic Construct

<400> SEQUENCE: 27
ggacgatgcc tggggcccaa cccagccttg tgcaaat                  37

<210> SEQ ID NO 28
<211> LENGTH: 32
<212> TYPE: DNA
<213> ORGANISM: Artificial Sequence
<220> FEATURE:
<223> OTHER INFORMATION: Synthetic Construct

<400> SEQUENCE: 28
ctggactgag ccccattcat cgtcctgctg ct                       32

<210> SEQ ID NO 29
<211> LENGTH: 32
<212> TYPE: DNA
<213> ORGANISM: Artificial Sequence
<220> FEATURE:
<223> OTHER INFORMATION: Synthetic Construct

<400> SEQUENCE: 29
agcagcagga cgatgaatgg ggctcagtcc ag                       32

<210> SEQ ID NO 30
<211> LENGTH: 32
<212> TYPE: DNA
<213> ORGANISM: Artificial Sequence
<220> FEATURE:
<223> OTHER INFORMATION: Synthetic Construct

<400> SEQUENCE: 30
ctggactgag ccccaggcat cgtcctgctg ct                       32

<210> SEQ ID NO 31
<211> LENGTH: 32
<212> TYPE: DNA
<213> ORGANISM: Artificial Sequence
<220> FEATURE:
<223> OTHER INFORMATION: Synthetic Construct

<400> SEQUENCE: 31
agcagcagga cgatgcctgg ggctcagtcc ag                               32

<210> SEQ ID NO 32
<211> LENGTH: 32
<212> TYPE: DNA
<213> ORGANISM: Artificial Sequence
<220> FEATURE:
<223> OTHER INFORMATION: Synthetic Construct

<400> SEQUENCE: 32
ctgggttggg ccccattcat cgtcctgctg ct                               32

<210> SEQ ID NO 33
<211> LENGTH: 32
<212> TYPE: DNA
<213> ORGANISM: Artificial Sequence
<220> FEATURE:
<223> OTHER INFORMATION: Synthetic Construct

<400> SEQUENCE: 33
agcagcagga cgatgaatgg ggcccaaccc ag                               32

<210> SEQ ID NO 34
<211> LENGTH: 32
<212> TYPE: DNA
<213> ORGANISM: Artificial Sequence
<220> FEATURE:
<223> OTHER INFORMATION: Synthetic Construct

<400> SEQUENCE: 34
ctgggttggg ccccaggcat cgtcctgctg ct                               32

<210> SEQ ID NO 35
<211> LENGTH: 32
<212> TYPE: DNA
<213> ORGANISM: Artificial Sequence
<220> FEATURE:
<223> OTHER INFORMATION: Synthetic Construct

<400> SEQUENCE: 35
agcagcagga cgatgcctgg ggcccaaccc ag                               32

<210> SEQ ID NO 36
<211> LENGTH: 30
<212> TYPE: DNA
<213> ORGANISM: Artificial Sequence
<220> FEATURE:
<223> OTHER INFORMATION: Synthetic Construct

<400> SEQUENCE: 36
ccaagcttgg ccgcagaccg tgcatcatga                                  30

<210> SEQ ID NO 37
<211> LENGTH: 31
<212> TYPE: DNA
<213> ORGANISM: Artificial Sequence
<220> FEATURE:
<223> OTHER INFORMATION: Synthetic Construct

<400> SEQUENCE: 37
catgccatgg catgcagctt gggccctcga g                                31

<210> SEQ ID NO 38
<211> LENGTH: 20
<212> TYPE: DNA

```
<213> ORGANISM: Artificial Sequence
<220> FEATURE:
<223> OTHER INFORMATION: Synthetic Construct

<400> SEQUENCE: 38
ggtgctttgt gaagggaaag                                                 20

<210> SEQ ID NO 39
<211> LENGTH: 20
<212> TYPE: DNA
<213> ORGANISM: Artificial Sequence
<220> FEATURE:
<223> OTHER INFORMATION: Synthetic Construct

<400> SEQUENCE: 39
gttgcaccac agatgaaacg                                                 20

<210> SEQ ID NO 40
<211> LENGTH: 2946
<212> TYPE: DNA
<213> ORGANISM: Homo sapiens

<400> SEQUENCE: 40
actccaaatt gcattatcga gaaacagaca acttgtttct tactctgcaa tgagccccctt     60 gcattgaatt ctcaagcacc tggattttgt tctgcatccg tctggtgcat ccttaaaaaa    120
aaaaaaaaat gcctgcgttc cacgctgcaa cctttatgcc cttcccagac ctttcttacc    180
ctcagctgta tttgctagac attctttatt tctgagtttg tatcttaaaa tattactgga    240
actttgtgct tagttcccaa gggacttgaa ctctcatgag ctctctggct catggcctgc    300
accccagatc tcccaaccca gggaccatta cccgggaaga ggattccaca gtgttctttt    360
ctgttcctag tgatagagaa catctaggat ctccttctg gctgcagagt cccgctttcc     420
cccatctcca tccttttctg ctccacgtaa caccttgaca tctctcattt taggggaatg    480
tggtagaaga ggaggggcag ccggttggct cattggaggt gtggggtttt ggcttttgg     540 ttttctggcc atgatgcata gttttattt tcatttctt cttgttcctt ccttctggct     600
ttatttttca agttgtactg cgtaccttag ggaagaagta tccaaaatcg tcaagtgctt    660
ctatttaaca atgaaaagta aaattgttgt gaggatcagc tcccattgat tctgatttta    720
ttaggttggt gcaaaagtaa ttgtggtttt tgccacgact ctttttttttt tgagacggag    780 tctcgctctg ttgcccaggt tagagtgcag tggcgcaatc tcggctcact gcaacctctg    840
cctcctgggt ttaagcgatt atcctgcctc acctactgag tagctgggat tataggtgcc    900
tgccactatg cctggctaat ttttgtattt tcagtagaga cagggtttcc ccatgttggc    960
caggctggtc tcgaactcct gacctcaagt gatccatccg cctcagactc ccaaagtgct   1020
gggatcacca gcctgagcca cggcacccgg ccgccatgac tccacaatta cttttgcacc   1080
aacctaataa atgttgtttg tgtttatcag tctctggtgt ctctcccttt cctgtctgcc   1140
tcctcttctc ctcgcttctt ataggtgtgt gtgttggggg ggtgggtggg gggtgcgttc   1200
tgatagaata acaaacagag gataccaagg aaatttttta aaaacccttt aacgaaagag   1260
agccaacatt gcatgaaggc tgagattttt tttttaaagg caaggattca gaaagggct    1320 gatcagtatt ttctgatcct agttcagtgc tagtcaggga gactgtcagt aaagaccttt   1380
ttggtctgtt gatttgtaga attaagcaaa agatgaccat gccctgtgg aagctgggtt    1440 ggtaccagct ggtagctgat ttcccaggag aaccctgaac gctttacaga tgatctactg   1500
actccaaaac aagacctgaa gcagcaaaca cttttacacc aaatgcgtct tcttttaatg   1560
```

```
tcttaaaata accttttcta tagtccttcc cttttgcaag gtcactgctg tagctcagca      1620
cttacccagt gcctctggct ccatgatgta gaatacgtgt gttttctcat tgttcctttt      1680
gcctctgttg ccgaatgttt ttaatgtgtt aactacaaaa cagagttgga ggaacttgga      1740
ttttatgaga tgctgtaccc tatctccccc aaccccccaa cacacagaca cacgccccca      1800
tgacttggaa ttcgggagat tttttcagt aatgattcaa cgtgatttgt gatggagaat       1860
tttaggcaca gcttgagatc aatgataagg gccctaaat caaggtgagc ttcccccacc       1920
tccgtgcact tgcattctgt gtgggcagga ggccctgccc tgaaaggggg ctccgtcctg      1980
tcaagagcct atggtttcaa gacttaaaca tctttgttgg aacttgcttg gaagaggggc      2040
ctgtgttgcc accttggaaa gaaagtttct ctgtcctttc agctggggt ggaggaggg       2100 ctgtggaagg gggcttgctg gcagttgagt tccaccaatg ttttctcaag ccgacactga     2160
gccccattca tcctcctgcc catgtgtggc tccggcaccc ctagacgggg ccagcccagc     2220
agcctgaagt ccgcatttag aacttgatcc cctcttataa cgattaaatt ttagtaagta    2280
aaataaaaat gcttcagaaa gaaaaaaaag aaggaagaa agagtggaac aatacttgtt     2340
ttatttaacg accagaactt tttgacaaca ccccccttcc ccgcaggata tgagaatgcc     2400
tggtccactg cagtccatcc ccagggacct cgaagcagaa tttggctgga ggggtgcgg    2460 ggggattct aatgtaaaca gtgaccctga agccctggag ccagttcccc cttctttccc    2520
ctgtctcccc ttctgtcttg ctgccccacc cccagcccca cacccccca ccccccccac  2580 ccccaccccg agacaaacac agaacactga gcaacttcag gttcaggcag gggaggaata   2640
aaggtgcttt gtaaaggga aggaaaacat tcctggggga ggtgagggct tggggcatga   2700
atgtgccctc agtctgggtg gacgctgcac acccagatgg gaggttgggg gggacgccga   2760
ggtggaggga ggagggccgg gccccagcca ggaagctctg gcgtgggca gggcttgtgg   2820 gaatgatttc attggaaagg cctgcgatat ttttttcccct cctgcgtgtg gttcttggag   2880
aaagttggag gtggtggtga tttcagtcgc cttggccgcc ttgagccgga gctgagcgga   2940
ggcact                                                                2946
```

<210> SEQ ID NO 41
<211> LENGTH: 807
<212> TYPE: DNA
<213> ORGANISM: Homo sapiens

<400> SEQUENCE: 41

```
gttttctcaa gccgacactg agccccattc atcctcctgc ccatgtgtgg ctccggcacc       60
cctagacggg gccagcccag cagcctgaag tccgcattta gaacttgatc ccctcttata     120
acgattaaat tttagtaagt aaaataaaaa tgcttcagaa agaaaaaaaa gaaggaagaa     180
aagagtggaa caatacttgt tttatttaac gaccagaact ttttgacaac accccccttc    240
cccgcaggat atgagaatgc ctggtccact gcagtccatc cccagggacc tcgaagcaga     300
atttggctgg aggggtgcg ggggggattc taatgtaaac agtgaccctg aagccctgga     360
gccagttccc ccttctttcc cctgtctccc cttctgtctt gctgccccac cccagcccc     420 aacaccccc accccccca ccccaccccc gagacaaaca cagaacactg agcaacttca     480
ggttcaggca ggggaggaat aaaggtgctt tgtaaagggg aaggaaaaca ttcctggggg    540
aggtgagggc ttggggcatg aatgtgccct cagtctgggt ggacgctgca cacccagatg    600
ggaggttggg ggggacgccg aggtggaggg aggagggccg ggccccagcc aggaagctct    660
```

```
gggcgtgggc agggcttgtg ggaatgattt cattggaaag gcctgcgata ttttttcccc      720
tcctgcgtgt ggttcttgga gaaagttgga ggtggtggtg atttcagtcg ccttggccgc      780
cttgagccgg agctgagcgg aggcact                                          807
```

```
<210> SEQ ID NO 42
<211> LENGTH: 36
<212> TYPE: DNA
<213> ORGANISM: Artificial Sequence
<220> FEATURE:
<223> OTHER INFORMATION: Synthetic Construct

<400> SEQUENCE: 42
cccagcttgg gactccaaat tgcattatcg agaaac                                36

<210> SEQ ID NO 43
<211> LENGTH: 34
<212> TYPE: DNA
<213> ORGANISM: Artificial Sequence
<220> FEATURE:
<223> OTHER INFORMATION: Synthetic Construct

<400> SEQUENCE: 43
catgccatgg catgagtgcc tccgctcagc tccg                                  34

<210> SEQ ID NO 44
<211> LENGTH: 35
<212> TYPE: DNA
<213> ORGANISM: Artificial Sequence
<220> FEATURE:
<223> OTHER INFORMATION: Synthetic Construct

<400> SEQUENCE: 44
cccaagcttg gggttttctc aagccgacac tgagc                                 35

<210> SEQ ID NO 45
<211> LENGTH: 34
<212> TYPE: DNA
<213> ORGANISM: Artificial Sequence
<220> FEATURE:
<223> OTHER INFORMATION: Synthetic Construct

<400> SEQUENCE: 45
catgccatgg catgagtgcc tccgctcagc tccg                                  34

<210> SEQ ID NO 46
<211> LENGTH: 17
<212> TYPE: DNA
<213> ORGANISM: Artificial Sequence
<220> FEATURE:
<223> OTHER INFORMATION: Synthetic Construct

<400> SEQUENCE: 46
gactgagccc caggcat                                                     17

<210> SEQ ID NO 47
<211> LENGTH: 17
<212> TYPE: DNA
<213> ORGANISM: Artificial Sequence
<220> FEATURE:
<223> OTHER INFORMATION: Synthetic Construct

<400> SEQUENCE: 47
ggttgggccc cattcat                                                     17
```

```
<210> SEQ ID NO 48
<211> LENGTH: 17
<212> TYPE: DNA
<213> ORGANISM: Artificial Sequence
<220> FEATURE:
<223> OTHER INFORMATION: Synthetic Construct

<400> SEQUENCE: 48
ggttgggccc caggcat                                                    17
```